(12) United States Patent
Finkelstein et al.

(10) Patent No.: US 7,915,423 B2
(45) Date of Patent: Mar. 29, 2011

(54) SOLID STATES OF PANTOPRAZOLE SODIUM, PROCESSES FOR PREPARING THEM AND PROCESSES FOR PREPARING KNOWN PANTOPRAZOLE SODIUM HYDRATES

(75) Inventors: Nina Finkelstein, Herzliya (IL); Barnaba Krochmal, Jerusalem (IL); Shlomit Wizel, Petah Tiqva (IL); Viviana Braude, Kadima (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 691 days.

(21) Appl. No.: 11/881,467

(22) Filed: Jul. 27, 2007

(65) Prior Publication Data
US 2008/0132707 A1    Jun. 5, 2008

Related U.S. Application Data

(62) Division of application No. 10/739,272, filed on Dec. 19, 2003, now Pat. No. 7,507,829.

(60) Provisional application No. 60/434,445, filed on Dec. 19, 2002, provisional application No. 60/453,836, filed on Mar. 12, 2003.

(51) Int. Cl.
C07D 401/12    (2006.01)
(52) U.S. Cl. .................................................. 546/273.7
(58) Field of Classification Search ................ 546/273.7
See application file for complete search history.

(56) References Cited

U.S. PATENT DOCUMENTS

| | | | |
|---|---|---|---|
| 4,508,905 A | 4/1985 | Junggren et al. |
| 4,555,518 A | 11/1985 | Rainer et al. |
| 4,628,098 A | 12/1986 | Nohara et al. |
| 4,758,579 A | 7/1988 | Kohl et al. |
| 5,045,552 A | 9/1991 | Souda et al. |
| 5,391,752 A | 2/1995 | Hoerrner et al. |
| 5,708,013 A | 1/1998 | Souda et al. |
| 6,017,560 A | 1/2000 | Makino et al. |
| 6,124,464 A | 9/2000 | Hogberg et al. |
| 6,313,303 B1 | 11/2001 | Tagami et al. |
| 6,410,569 B1 | 6/2002 | Kohl |
| 6,423,846 B1 | 7/2002 | Moon et al. |
| 6,545,024 B1 | 4/2003 | Tsujii et al. |
| 6,686,379 B2 | 2/2004 | Kohl |
| 6,723,852 B2 | 4/2004 | Maimo et al. |
| 6,933,389 B2 | 8/2005 | Reddy et al. |
| 7,081,534 B2 | 7/2006 | Napoletano et al. |
| 7,105,681 B2 | 9/2006 | Turchetta et al. |
| 7,169,799 B2 * | 1/2007 | Hashimoto et al. ............ 514/341 |
| 7,176,319 B2 | 2/2007 | Reddy et al. |
| 7,256,297 B2 | 8/2007 | Senanayake et al. |
| 2003/0036554 A1 | 2/2003 | Avrutov et al. |
| 2003/0083517 A1 | 5/2003 | Senanayake et al. |
| 2004/0138466 A1 | 7/2004 | Avrutov et al. |
| 2004/0158072 A1 | 8/2004 | Loebermann et al. |
| 2004/0177804 A1 | 9/2004 | Finkelstein et al. |
| 2004/0235904 A1 | 11/2004 | Finkelstein et al. |
| 2004/0248940 A1 | 12/2004 | Kromer et al. |
| 2005/0004172 A1 | 1/2005 | Filic et al. |
| 2005/0075370 A1 | 4/2005 | Braude et al. |
| 2005/0245578 A1 | 11/2005 | Allegrini et al. |
| 2005/0288334 A1 | 12/2005 | Kohl et al. |
| 2006/0167262 A1 | 7/2006 | Kohl et al. |
| 2007/0249662 A1 | 10/2007 | Allegrini et al. |
| 2008/0004319 A1 | 1/2008 | Braude et al. |
| 2008/0167473 A1 | 7/2008 | Coppi et al. |
| 2009/0005570 A1 | 1/2009 | Fan |

FOREIGN PATENT DOCUMENTS

| | | |
|---|---|---|
| CA | 1254215 | 5/1989 |
| CN | 101 250 180 | 8/2008 |
| CN | 101 250 181 | 8/2008 |
| DE | 40 35 455 | 5/1992 |
| EP | 302720 | 2/1989 |
| EP | 484265 | 5/1992 |
| EP | 0 533 264 | 3/1993 |
| EP | 0533790 | 3/1993 |
| EP | 1 270 555 | 1/2003 |
| EP | 1277752 | 1/2003 |
| EP | 1 306 375 | 5/2003 |
| EP | 1476441 | 11/2004 |
| EP | 1921075 | 5/2008 |
| EP | 1992619 | 11/2008 |
| ES | 860 2765 | 3/1986 |
| ES | 860 4929 | 8/1986 |
| ES | 870 3868 | 5/1987 |
| GB | 2 134 523 | 8/1984 |
| WO | WO 91/19710 | 12/1991 |
| WO | WO 96/02535 | 2/1996 |
| WO | WO 98/40377 | 9/1998 |
| WO | WO 98/40378 | 9/1998 |
| WO | WO 99/47514 | 9/1999 |
| WO | WO 00/10995 | 3/2000 |
| WO | WO 01/04109 | 1/2001 |
| WO | WO 01/21617 | 3/2001 |

(Continued)

OTHER PUBLICATIONS

Kohl et al., "(H+,K+)-ATPase Inhibiting, etc.," Journal of Medicinal Chemistry, 35,(5), 1992, 1049-1057.*

(Continued)

Primary Examiner — Patricia L Morris
(74) Attorney, Agent, or Firm — Kenyon & Kenyon LLP

(57) ABSTRACT

Crystalline pantoprazole sodium Forms II, IV, V, VI, VIII, IX, X, XI, XII, XIII, XIV, XV, XVI, XVII, XVIII, XIX and XX; pantoprazole sodium solvates containing water, acetone, butanol, methylethylketone, dimethylcarbonate, propanol and 2-methylpropanol; and amorphous pantoprazole sodium are disclosed.

7 Claims, 18 Drawing Sheets

FOREIGN PATENT DOCUMENTS

| | | |
|---|---|---|
| WO | WO 01/083473 | 11/2001 |
| WO | WO 02/28852 | 4/2002 |
| WO | WO 02/062786 | 8/2002 |
| WO | WO 03/062223 | 7/2003 |
| WO | WO 03/089408 | 10/2003 |
| WO | WO 2004/035052 | 4/2004 |
| WO | WO 2004/052881 | 6/2004 |
| WO | WO 2004/056804 | 7/2004 |
| WO | WO 2004/080961 | 9/2004 |
| WO | WO 2004/099183 | 11/2004 |
| WO | WO 2005/011692 | 2/2005 |
| WO | WO 2007/036771 | 4/2007 |
| WO | WO 2007/041790 | 4/2007 |
| WO | WO 2007/086077 | 8/2007 |
| WO | WO 2007/129328 | 11/2007 |
| WO | WO 2009/010937 | 1/2009 |
| WO | WO 2009/066317 | 5/2009 |
| WO | WO 2009/075516 | 6/2009 |

OTHER PUBLICATIONS

Kotar-Jordan et al., "Solid State, etc.," Farm. Vestn, 2003:54 (2), 411-412.*

Kirk-Ohmer Encyclopedia of Chemical Technology Copyright 2002 by John Wiley & Sons, Inc., pp. 95-147, Artlical Online Posting date: Aug. 16, 2002.*

Third Party Observation, dated Jan. 30, 2008, from corresponding European Patent Application No. 04755278.1 filed Jun. 10, 2004.

Third Party Observation, dated Jun. 3, 2008, from corresponding European Patent Application No. 04755278.1 filed Jun. 10, 2004.

Garner, A., et al., "Pantoprazole: A New and More Specific Proton Pump Inhibitor,"*Expert Opinion on Investigational Drugs*. 6(7): 885-893 (1997).

Graul A., et al: "Esomeprazone Magnesium(−)-Omeprazole Magnesium Perprazole (formerly) (S)-Omeprazole Magnesium H-199/18 Nexium™", *Drugs of the Future*. 24(11): 1178-1183 (1999).

Moustafa, "Spectrophotometric methods for the determination of lansoprazole and pantoprazole sodium sesquihydrate," *Journal of Pharmaceutical and Biomedical Analysis*, 22: 45-58 (2000).

Otsuka et al., "Effect of Polymorphic Forms of Bulk Powders on Pharmaceutical Properties of Carbamazepine Granules," *Chem. Pharm. Bull.*, 47(6): 852-856 (1999).

Patai, et al., The Chemistry of Sulphones and Sulphoxides, 249 (J. Wiley & Sons: New York 1988).

Vyas K., et al. "Lansoprazole, An Antiulcerative Drug," *Acta Crystalographica Section C, Crystal Structure Communications*, C56(12): E572-E573 (2000).

Williams M.P., et al., "Review Article: The Pharmacology of Rabeprazole," *Alimentary Pharmacology & Therapeutics*, 13(3):3-10 (1999).

Merck Index, 13th ed., p. 1256, compound 7084 (2001).

A. Badwan et al. "Pantoprazola Sodium" Analytical Profiles of Drugs Substances and Excipients, Paragraph '03.4, Table 1; vol. 29, 2002.

Kotar-Jordan, B. "Solid State Characterisation of New Pantoprazole Sodium Hydrate Forms" Farm. Vestn. pp. 411-412. vol. 54, No. 2, 2003.

Kohl, B., et al., "($H^+$, $K^+$)-ATPase Inhibiting 2-[(2-Pyridylmethyl sulfonyl]benzimidazoles. A Novel Series of Dimethoxypyridyl-Substituted Inhibitors with Enhanced Selectivity. The Selection of Pantoprazole as a Clinical Candidate.", Journal of Medical Chemistry, vol. 35, No. 5, Mar. 6, 1992.

Third Party Observation, dated Jun. 17, 2009, from corresponding European Patent Application No. 0700422.5 filed Mar. 1, 2007.

Badwan, A. et al. "Pantoprazole Sodium" *Analytical Profiles of Drugs Substances and Excipients*, vol. 29, No. 1, pp. 213-259 (2002).

Brittain et al., "Polymorphism in Pharmaceutical Solids," NY: Marcel Dekker, Inc. 1999, pp. 183-226.

Brittain, H.G., "Polymorphism in Pharmaceutical Solids," 1999, pp. 235-238.

Drabowicz et al., Synthesis of Sulphoxides; in Rappoport et al. The Chemistry of Sulphones and Sulphoxides. p. 249 (J. Wiley & Sons: New York 1988).

Drabowicz et al., Organic Preparations and Procedures Int. 14(1-2), 45-89 (1982).

* cited by examiner

SOLID STATES OF PANTOPRAZOLE SODIUM, PROCESSES FOR PREPARING THEM AND PROCESSES FOR PREPARING KNOWN PANTOPRAZOLE SODIUM HYDRATES

CROSS-REFERENCE TO RELATED APPLICATION

This application is a divisional of U.S. application Ser. No. 10/739,272, filed Dec. 19, 2003 now U.S. Pat. No. 7,507,829, which claims the benefit of U.S. Provisional Application Ser. Nos. 60/434,445, filed on Dec. 19, 2002 and 60/453,836, filed Mar. 12, 2003, hereby incorporated by reference.

FIELD OF THE INVENTION

The present invention relates to the gastric acid secretion inhibitor pantoprazole in the solid state and, more particularly, to crystalline and amorphous forms of pantoprazole sodium having unique physical properties as well as processes for preparing them, pharmaceutical compositions containing them and methods of treating gastroesophageal reflux disease using them.

BACKGROUND OF THE INVENTION

Pantoprazole is a gastric acid secretion inhibitor. The systematic chemical name of pantoprazole is 5-(difluoromethoxy)-2-[[(3,4-dimethoxy-2-pyridinyl)methyl]sulfinyl]-1H-benzimidazole and its molecular structure is represented by formula (I).

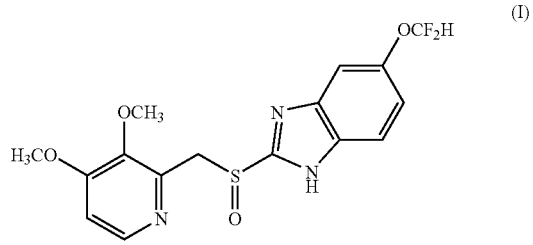

U.S. Pat. No. 4,758,579 discloses that pantoprazole and many other fluoroalkoxy substituted benzimidazoles are gastric acid secretion inhibitors. The '579 patent states that pantoprazole can be prepared by oxidation of the sulfide analog with meta-chloroperbenzoic acid by following a procedure described in Example 2 of the '579 patent. According to Example 2, the oxidation is conducted in dichloromethane. The reaction mixture is quenched with sodium thiosulfate and sodium carbonate. The product is extracted from the aqueous phases with dichloromethane, washed with sodium thiosulfate, dried over magnesium sulfate and concentrated. The residue is then crystallized from diisopropyl ether and recrystallized from a mixture of dichloromethane and diisopropyl ether. Although pantoprazole sodium is the subject of a claim in the '579 patent, a detailed procedure for converting pantoprazole to its sodium salt is not set forth in the '579 patent.

Kohl, B. et al. *J. Med. Chem.* 1992, 35, 1049-57 reports a study of the inhibitor activity and pH dependent stability of a series of dimethoxypyridyl-substituted methylsulfinylbenzimidazoles, including pantoprazole. Pantoprazole sodium sesquihydrate was prepared by adding 6 N NaOH to a solution of pantoprazole in a 6:1 ethanol:dichloromethane mixture at 20° C. After 10 minutes, diisopropyl ether was added until the mixture became turbid. After stirring for another two hours, the precipitate was collected by filtration, washed with isopropyl ether and dried under vacuum at 40° C. The results of C, H, N and S analysis, coupled with the anticipated structure and molecular formula of pantoprazole indicated that the product contained 6.5% water, corresponding to a sesquihydrate (1.5 mol./mol.) level of hydration.

International Publication No. WO 91/19710 discloses a monohydrate form of pantoprazole sodium. The monohydrate form obtained by following the teachings of the '710 publication crystallizes as small cubic crystals, has a melting point of 150-153° C. and dissolves with difficulty in acetone. According to the '710 publication, the sesquihydrate contains 6.0-6.5% water and has a melting point of 137-140° C. The pantoprazole sodium monohydrate of the '710 publication can be made by dissolving pantoprazole in acetone or another low ketone and adding sodium hydroxide solution to the mixture. The monohydrate is obtained immediately in pure form after adding the sodium hydroxide solution. Alternatively, the monohydrate of the '710 publication can be obtained by crystallization from a solution prepared by dissolving pantoprazole sodium sesquihydrate in acetone or other lower ketone.

Pantoprazole is the active ingredient of a pharmaceutical product that is marketed in the United States by Wyeth-Ayerst Inc. under the brand name Protonix®. Protonix® is approved by the U.S. Food and Drug Administration for short term treatment of erosive esophagitis associated with gastroesophageal reflux disease ("GERD"), maintenance of healing of erosive esophagitis and pathological hypersecretory conditions including Zollinger-Ellison syndrome. According to the package insert for Protonix®, the product contains a monosodium salt of pantoprazole (hereafter "pantoprazole sodium") in a sesquihydrate state of hydration.

The present invention relates to the solid state physical properties of pantoprazole sodium Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by powder X-ray crystallography ("PXRD"), solid state $^{13}$C NMR spectrometry and infrared spectrometry.

These spectroscopic and utilitarian properties can be influenced by controlling the conditions under which a compound is obtained in solid form. There is a wide variety of techniques that have the potential of producing different crystalline forms of a compound. Examples include crystallization, crystal digestion, sublimation and thermal treatment. However, none of these techniques can be expected a priori to produce a new solid state form of a compound.

The present invention also relates to solvates of pantoprazole sodium. When a substance crystallizes out of solution, it may trap molecules of solvent at regular intervals in the crystal lattice. Solvation also affects utilitarian physical properties of the solid state like flowability and dissolution rate.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. New polymorphic forms and solvates of pantoprazole have now been discovered.

SUMMARY OF THE INVENTION

Accordingly, the present invention provides new crystalline forms of pantoprazole sodium and amorphous pantoprazole sodium, solvates and hydrates thereof.

In one aspect, the present invention provides pantoprazole sodium hydrates containing between about 7% to about 30% water (indicated by a LOD).

In another aspect, the present invention provides pantoprazole sodium Form II, characterized by a PXRD pattern having peaks at 16.6, 16.9, 17.5, 21.3, 21.7 and 22.2±0.2 degrees two-theta.

In another aspect, the present invention provides pantoprazole sodium acetone solvate.

In another aspect, the present invention provides pantoprazole sodium Form IV, which has produced a PXRD pattern having peaks at 5.5, 13.8, 16.5, 17.0, 26.2 and 26.6±0.2 degrees two-theta.

In another aspect, the present invention provides pantoprazole sodium butanol solvate.

In another aspect, the present invention provides pantoprazole sodium Form V, which has produced a PXRD pattern having peaks at 5.8, 12.3, 19.2, 19.7, 20.3 and 20.7±0.2 degrees two-theta.

In another aspect, the present invention provides pantoprazole sodium Form VI, characterized by a PXRD pattern having peaks at 17.9, 19.5, 20.4, 21.4, 24.6±0.2 degrees two-theta.

In another aspect, the present invention provides pantoprazole sodium methylethylketone solvate.

In another aspect, the present invention provides pantoprazole sodium Form VIII, which has produced a PXRD pattern having peaks at 5.6, 12.1, 13.0, 13.7±0.2 degrees two-theta.

In another aspect, the present invention provides pantoprazole sodium dimethylcarbonate solvate.

In another aspect, the present invention provides pantoprazole sodium Form IX, which has produced a PXRD pattern having peaks at 5.3, 13.6, 16.9, 17.3±0.2 degrees two-theta.

In another aspect, the present invention provides pantoprazole sodium propanol solvate.

In another aspect, the present invention provides pantoprazole sodium Form X, which has produced a PXRD pattern having peaks at 16.4, 18.3, 19.0, 19.7, 21.9±0.2 degrees two-theta.

In another aspect, the present invention provides anhydrous pantoprazole sodium.

In another aspect, the present invention provides pantoprazole sodium Form XI, characterized by a PXRD pattern having peaks at 6.0, 16.0, 24.4, 25.1, 25.8±0.2 degrees two-theta.

In another aspect, the present invention provides pantoprazole sodium 2-methylpropanol solvate.

In another aspect, the present invention provides pantoprazole sodium Form XII, which has produced a PXRD pattern having peaks at 5.6, 15.7, 19.4, 24.7, 28.3±0.2 degrees two-theta.

In another aspect, the present invention provides pantoprazole sodium Form XIII, characterized by a PXRD pattern having peaks at 6.7, 15.9, 23.6, 27.7, 29.3, 30.6±0.2 degrees two-theta.

In another aspect, the present invention provides pantoprazole sodium Form XIV, characterized by a PXRD pattern having peaks at 5.7, 17.0, 18.1, 22.7 and 25.8±0.2 degrees two-theta.

In another aspect, the present invention provides pantoprazole sodium Form XV, characterized by a PXRD pattern having peaks at 20.7, 21.4, 21.8 and 23.3±0.2 degrees two-theta.

In another aspect, the present invention provides pantoprazole sodium Form XVI, characterized by a PXRD pattern having peaks at 20.7, 21.4, 21.8 and 23.3±0.2 degrees two-theta.

In another aspect, the present invention provides pantoprazole sodium hydrate-methylethylketone solvate.

In another aspect, the present invention provides pantoprazole sodium Form XVII, which has produced a PXRD pattern having peaks at 15.2, 15.7, 25.8, and 26.5±0.2 degrees two-theta.

In another aspect, the present invention provides pantoprazole sodium hydrate-acetone solvate.

In another aspect, the present invention provides pantoprazole sodium Form XVIII, which has produced a PXRD pattern having peaks at 11.2, 13.2, 13.5, 13.8, 14.1±0.2 degrees two-theta.

In another aspect, the present invention provides pantoprazole sodium dihydrate.

In another aspect, the present invention provides pantoprazole sodium Form XIX, which has produced a PXRD pattern having peaks at 11.3, 13.4, 13.8, 26.2 and 26.6±0.2 degrees two-theta.

In another aspect, the present invention provides pantoprazole sodium trihydrate.

In another aspect, the present invention provides pantoprazole sodium Form XX, which has produced a PXRD pattern having peaks at 15.4, 17.9, 24.6, 25.9, 26.2, and 26.5±0.2 degrees two-theta.

In another aspect, the present invention provides amorphous pantoprazole sodium.

Pantoprazole sodium monohydrate can be prepared by precipitation of pantoprazole sodium from a solution in selected diluents wherein the solution is prepared by add pantoprazole and sodium hydroxide to the diluent. In another process a heterogeneous mixture of pantoprazole sodium and either dimethylcarbonate or acetone and pantoprazole sodium is separated from the heterogeneous mixture and recovered as pantoprazole sodium Form I.

Pantoprazole sodium sesquihydrate can be prepared by forming a solution of pantoprazole and sodium hydroxide in a selected diluent and precipitating crystals of the sesquihydrate from the solution. In addition, the sesquihydrate can be prepared by forming a heterogeneous mixture of pantoprazole sodium in a selected solvent and recovering the sesquihydrate from the mixture.

The present invention further provides processes for preparing known pantoprazole sodium monohydrate and sesquihydrate.

DETAILED DESCRIPTION OF THE PREFERRED EMBODIMENTS

The present invention provides seventeen novel crystalline solids of pantoprazole sodium that have been denominated Forms II, IV, V, VI, VIII, IX, X, XI, XII, XIII, XIV, XV, XVI, XVII, XVIII, XIX, XX and amorphous pantoprazole sodium. The novel forms of pantoprazole sodium produce unique PXRD patterns which can be used to identify and distinguish each of the novel forms from each other and known pantoprazole sodium Form I (monohydrate) and known pantoprazole sodium sesquihydrate.

The PXRD patterns depicted in the accompanying figures were obtained on a Scintag X-Ray powder diffractometer model X'TRA with a copper tube solid state detector. A round standard aluminum sample holder with round zero background quartz plate was used. Scanning parameters: Range: 2-40°2θ: continuous scan, Rate: 3 deg./min.

The present invention also provides acetone, butanol, methylethylketone, dimethylcarbonate, propanol and 2-methylpropanol solvates of pantoprazole sodium.

The present invention also provides hydrates of pantoprazole sodium containing between about 7% and about 30% water (as indicated by LOD).

The present invention also provides hydrate-methylethylketone solvate and hydrate-acetone solvate of pantoprazole sodium.

The present invention also provides anhydrous pantoprazole sodium.

The degree to which they are solvated was assessed by thermogravimetric analysis ("TGA"). The loss on drying ("LOD") of each of the solvated forms was measured by TGA using A Mettler TG50: Sample weight: 7-15 mg, heating rate: 10° C./min. Standard Alumina crucibles were used. Water contents were measured by Karl-Fisher titration method.

As used herein, the term "treating" refers to dissolving, granulating, slurrying or exposing to vapor.

Pantoprazole Sodium Form II

In a first aspect, the present invention provides a novel crystalline solid form of pantoprazole sodium that has been denominated Form II. This form can also exist as a hydrate. The hydration level is indicated by a LOD of 5-7% on heating from 25° C. to 170° C. and Karl Fisher analysis.

Figure 1:
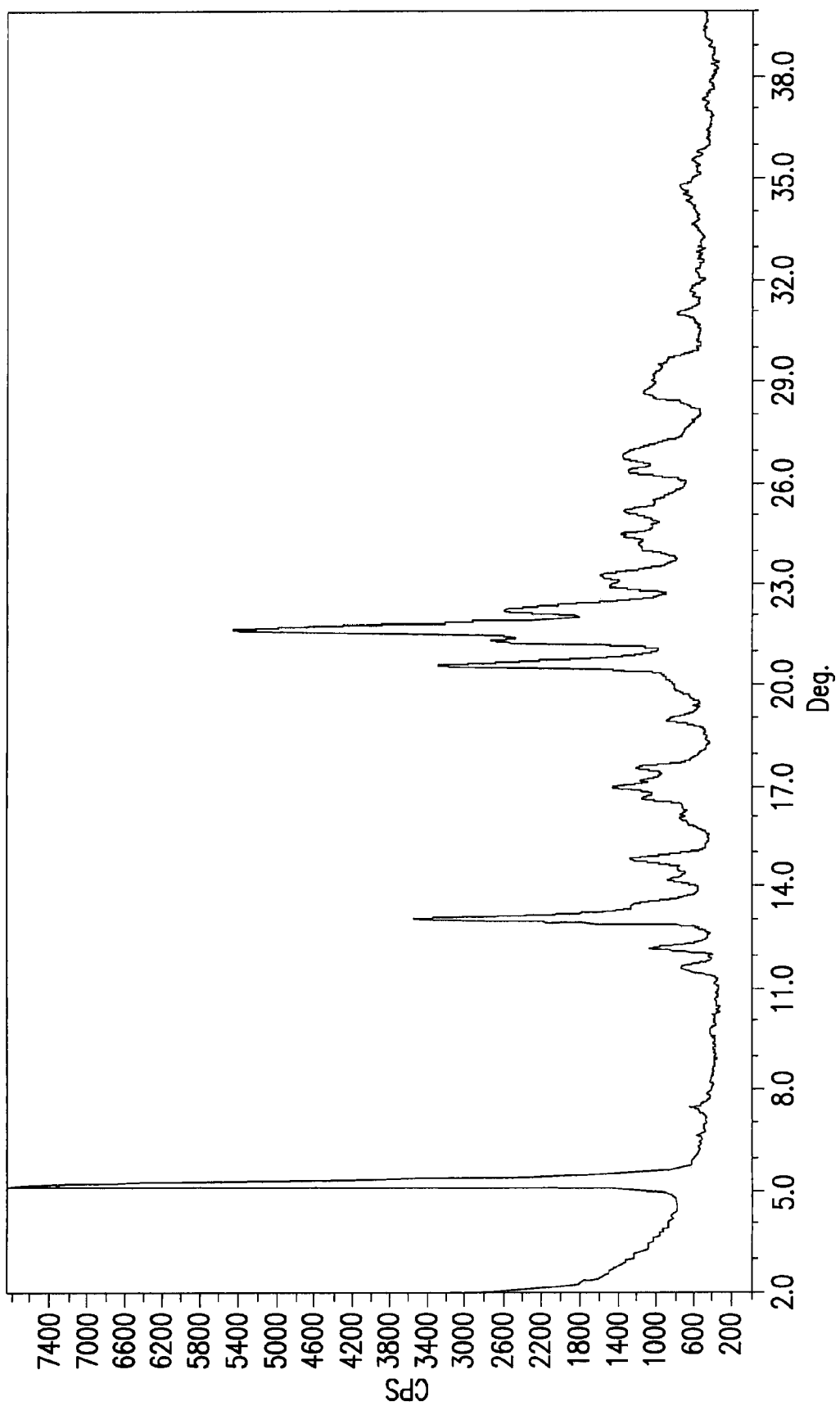
FIG. 1 is a representative PXRD pattern of pantoprazole sodium Form II.

Pantoprazole sodium Form II can be differentiated from other hydrated forms by its PXRD pattern, a representative example of which is provided in the diffractogram of FIG. 1. Particularly characteristic peaks in the PXRD pattern occur at 16.6, 16.9, 17.5, 21.3, 21.7 and 22.2±0.2 degrees two-theta. Additional peaks occur at 111.6, 12.2, 13.1, 14.2, 14.8, 20.6, 22.9 and 23.3±0.2 degrees two-theta.

Pantoprazole sodium Form II can be prepared by forming a solution of pantoprazole and excess sodium hydroxide in acetone and crystallizing Form II from the solution. Preferably, pantoprazole is added as the free base, though the sodium salt may be used. Excess sodium hydroxide is conveniently added as a concentrated aqueous NaOH solution. Sodium hydroxide should be added in an amount of from about 1 to about 2 molar equivalents with respect to pantoprazole. In a particularly preferred procedure, pantoprazole is dissolved in about 3-6 volumes of acetone. The solution is cooled to about 0° C. Then, the concentrated NaOH solution is added. Crystallization of the novel form of pantoprazole sodium is substantially complete within about 1-5 hours. The crystals can then be separated from the acetone by conventional means, such as by filtering or decanting and they may be washed, preferably with acetone.

In this disclosure, sodium hydroxide is commonly used as a source of sodium ions. However, it will be appreciated by those skilled in the art that other sources of sodium ion may be substituted for sodium hydroxide, such as sodium hydride, sodium methoxide, sodium ethoxide, sodium propoxide, sodium isopropoxide, sodium butoxide, sodium isobutoxide and sodium t-butoxide and the like.

Pantoprazole Sodium Form IV

Another aspect of this invention is a novel crystalline solid of pantoprazole sodium that can be obtained by contacting with acetone under certain controlled conditions. This crystalline solid has been denominated Form IV.

Figure 2:
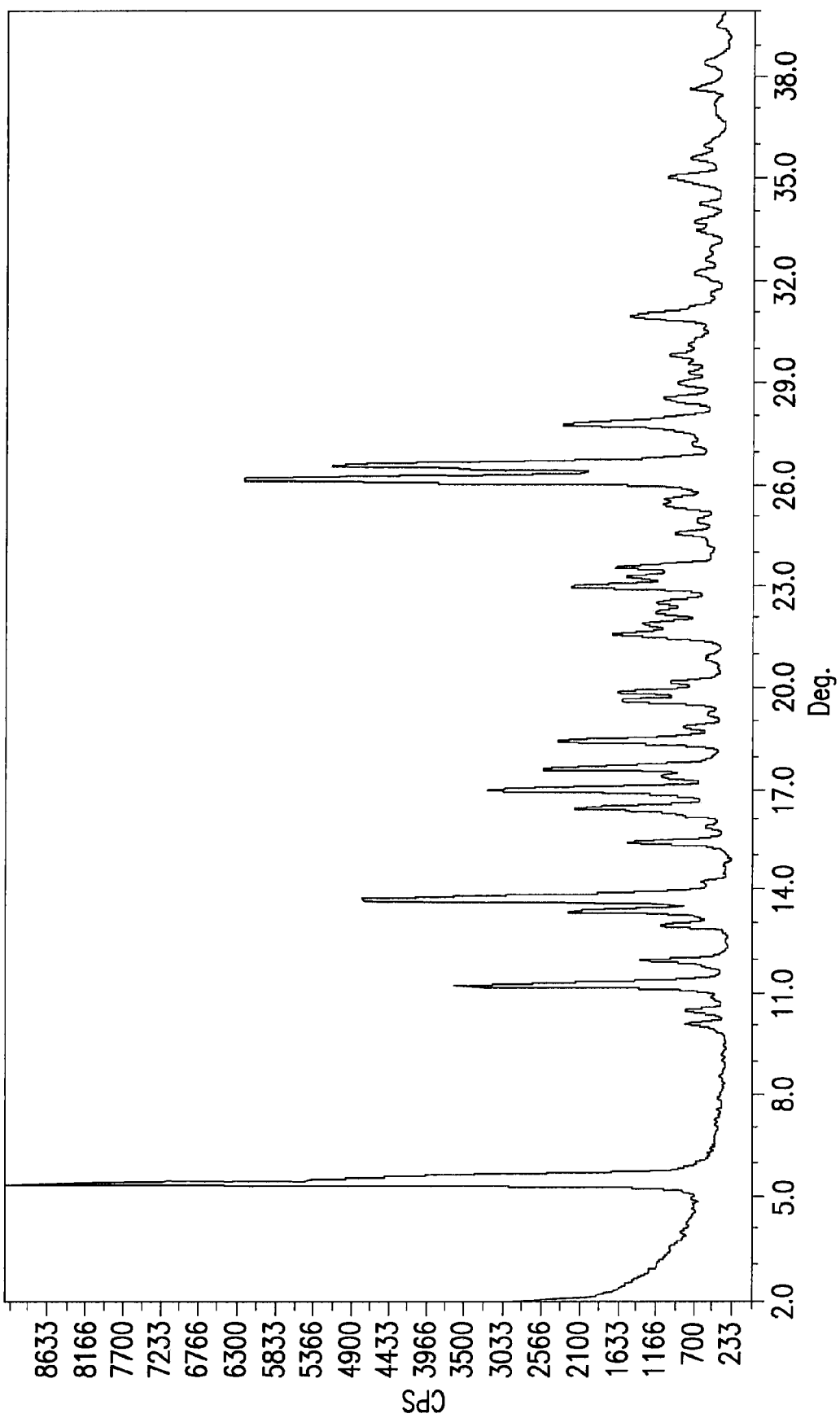
FIG. 2 is a representative PXRD pattern of pantoprazole sodium Form IV.

Pantoprazole sodium Form IV can be identified by its PXRD pattern, a representative example of which is provided in the diffractogram of FIG. 2. The acetone solvate is characterized by PXRD peaks at: 5.5, 13.8, 16.5, 17.0, 26.2 and 26.6±0.2 degrees two-theta. Additional peaks occur at 10.1, 10.5, 11.3, 12.0, 13.4, 15.4, 17.6, 18.4, 19.6, 19.9, 23.0, 23.5, 27.9±0.2 degrees two-theta.

Different samples of pantoprazole sodium Form IV have yielded different degrees of weight loss on heating. The most frequently observed loss is about 11-12 weight % when the sample is heated to 115° C., though LODs have varied from 10-30%. Form IV also contains water.

Pantoprazole sodium Form IV can be prepared by treating pantoprazole sodium Form II in acetone followed by crystallization without drying or by other means of contacting pantoprazole sodium Form II with acetone which are effective to induce the solid state conversion of Form II to Form IV. Generally, such conditions include techniques that involve forming a heterogeneous mixture of the Form II crystals and acetone. Such techniques include without limitation those known to the skilled artisan as slurrying, suspending, granulating, triturating and digesting. Hereafter, the formation of a heterogenous mixture of a solid and a liquid includes all of these techniques and does not limit the proportion of solid and liquid used in any way. In addition, Form IV can be prepared by contact of Form II with acetone vapors. Accordingly, as used in this disclosure the formation of a heterogeneous mixture also includes solid:gas mixtures. The existence of a solid:gas mixture is easily ascertained by those in the art since the gas is confined and in fluid communication with the crystals. Confinement and fluid communication may occur in a single vessel, but a single vessel is not strictly necessary since multiple containers that hold the crystals and the gas may be connected by pipes.

A particularly preferred process for preparing Form IV, wherein a heterogenous mixture of pantoprazole sodium Form II with acetone, preferably in a ratio of 1:10 (w/w) or greater, is agitated at room temperature for 8-12 h (e.g. overnight), is effective in converting substantially all of the Form II crystals to Form IV. Although a greater proportion of acetone may be used, the yield of crystals is likely to suffer unless steps are taken to drive dissolved pantoprazole out of solution such as cooling or adding an antisolvent in which pantoprazole sodium is insoluble or only sparingly soluble.

Pantoprazole sodium Form IV also is accessible starting with amorphous pantoprazole sodium (described below) using generally the same techniques used to convert Form II to Form IV. In particular, Form IV may be prepared by forming a heterogeneous mixture of amorphous pantoprazole sodium in acetone, and maintaining contact preferably for 30 minutes or more and then separating the solid from acetone, such as by filtering or decanting. The conversion of the amorphous form into Form IV is easily followed because the conversion of the amorphous powder to fine crystals can be observed with the naked eye. A preferred acetone:solid ratio for the process is 2:1 or less (resulting in a mixture commonly known as a slurry). A greater solvent:solid ratio (e.g. 4:1) tends to result in a lower low yield without an offsetting advantage such as acceleration of the conversion. The obtained crystals may be optionally dried gently at a temperature of up to 60° C., more preferably up to 40° C., for about 0-1 h, more preferably up to 30 min. However, drying at significantly higher temperature or for a considerably longer time may cause desolvation of the Form IV crystals into monohydrate crystals.

Pantoprazole Sodium Acetone Solvate

Another aspect of this invention is crystalline pantoprazole sodium acetone solvate.

Pantoprazole sodium acetone solvate can be prepared by treating pantoprazole sodium Form II with acetone followed by crystallization without drying or by other means of contacting pantoprazole sodium Form II with acetone which are effective to induce the solid state conversion of Form II to an acetone solvate.

In addition, an acetone solvate can be prepared by contact of Form II with acetone vapors.

In a particularly preferred process for preparing an acetone solvate, a heterogenous mixture of pantoprazole sodium Form II and acetone, preferably in a Form II:acetone ratio of 1:10 (w/w) or greater, is agitated at room temperature for 8-12 h. These conditions are generally effective in converting substantially all of the Form II crystals to an acetone solvate.

Pantoprazole sodium acetone solvate also is accessible starting with amorphous pantoprazole sodium (described below) using generally the same techniques used to convert Form II to an acetone solvate.

Pantoprazole Sodium Form V

Another aspect of the present invention is a novel crystalline solid of pantoprazole sodium that can be obtained by contacting with 1-butanol under certain controlled conditions. This crystalline solid has been denominated Form V.

Figure 3:
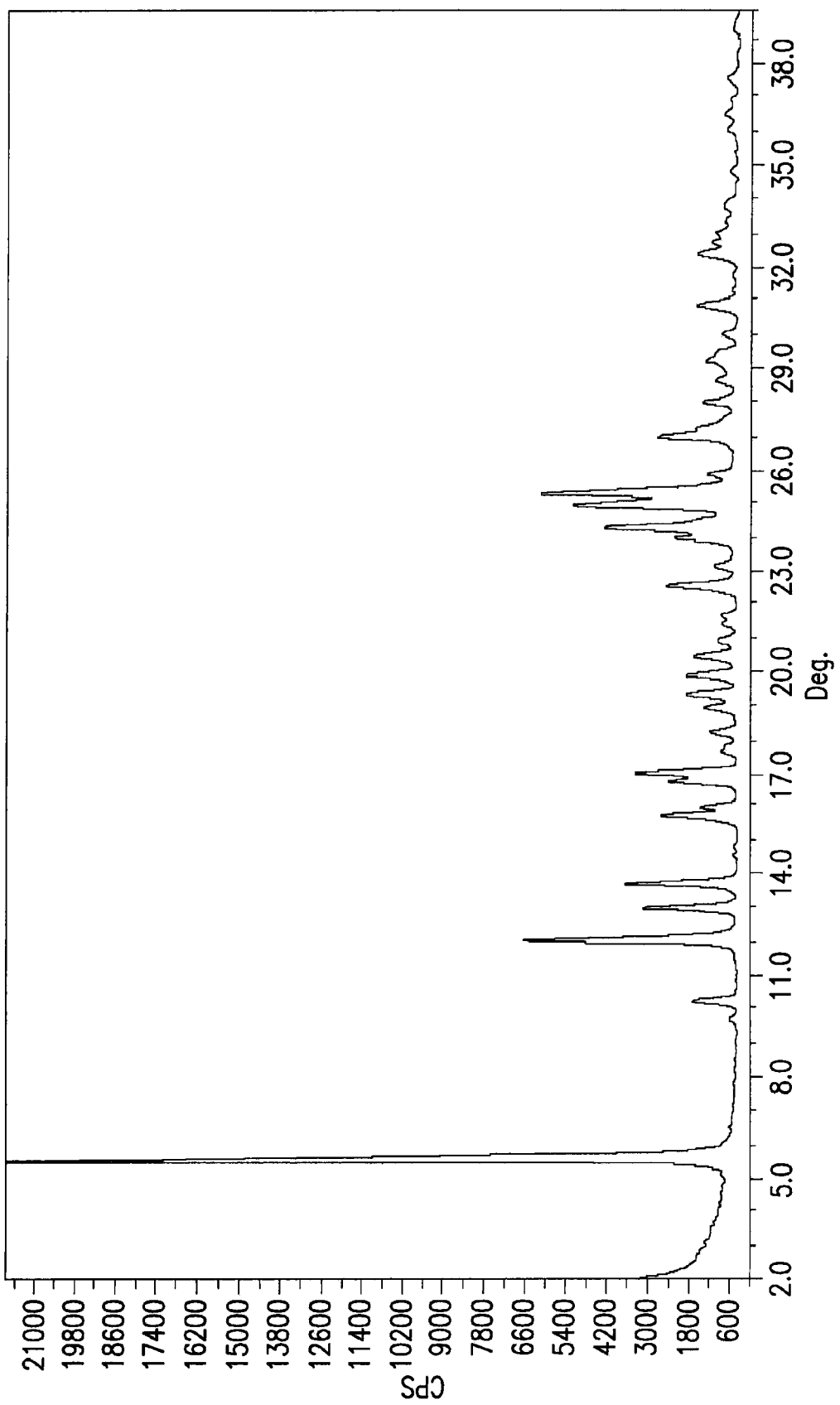
FIG. 3 is a representative PXRD pattern of pantoprazole sodium Form V.

Pantoprazole sodium Form V can be identified by its PXRD pattern, a representative example of which is provided in the diffractogram of FIG. 3. The 1-butanol solvate is characterized by PXRD peaks at 5.8, 12.3, 19.2, 19.7, 20.3 and 20.7±0.2 degrees two-theta. Additional peaks occur at: 13.3, 14.0, 16.0, 17.1, 18.6, 22.8, 24.3, 25.3, 25.8±0.2 degrees two-theta.

Samples of pantoprazole sodium Form V lose about 8-30% of their weight when heated up to 160° C. Typically they lose about 10 to 12% of their weight when heated to 160° C. Karl Fisher analysis shows that this 1-butanol solvate can contain about 15% water.

Pantoprazole sodium is appreciably soluble in 1-butanol. Accordingly, initial investigation focused on how this solvate could be produced by crystallization from a solution rather than a heterogeneous technique. We discovered that combining free pantoprazole and solid sodium hydroxide in 1-butanol and crystallization of the resulting pantoprazole sodium salt yielded Form V. The presence of minor amounts of water originating from the use of non-anhydrous 1-butanol, a hydrated starting material or water adsorbed on the equipment used for crystallization has no effect on the crystal form obtained.

In addition, we discovered that Form V can be prepared by exposing crystals of pantoprazole sodium Form II, to 1-butanol vapors at room temperature. The conversion can be effected in a few of weeks, though more elevated temperatures may accelerate the conversion.

The obtained Form V crystals may be optionally dried gently at a temperature of up to 60° C., more preferably up to 40° C., for about 0-1 h, more preferably up to 30 min. More vigorous drying at higher temperature or more time, tends to cause the transformation of Form V crystals into Form XIII crystals.

Pantoprazole Sodium Butanol Solvate

Another aspect of the present invention is crystalline pantoprazole sodium butanol solvate. Pantoprazole sodium butanol solvate is obtained by combining free pantoprazole and solid sodium hydroxide in 1-butanol and crystallizing the resulting pantoprazole sodium salt. In addition, we discovered that a butanol solvate can be prepared by exposing crystals of pantoprazole sodium Form II, to 1-butanol vapors at room temperature.

Pantoprazole Sodium Form VI

Another aspect of this invention is a novel crystalline solid of pantoprazole sodium that can be obtained by contacting with water under certain controlled conditions. This crystalline solid has been denominated Form VI. This form can also exist as a hydrate.

Figure 4:
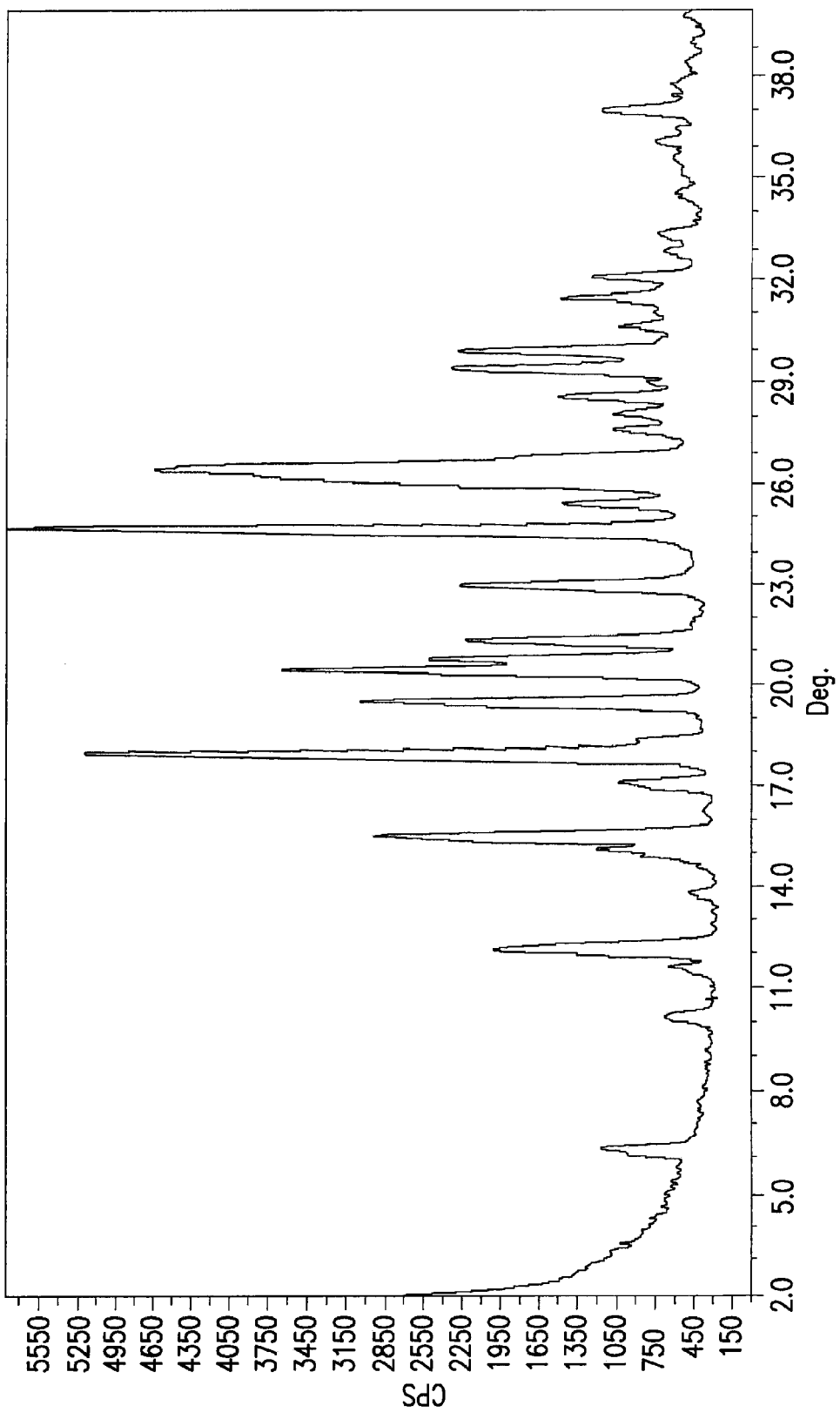
FIG. 4 is a representative PXRD pattern of pantoprazole sodium Form VI.

Pantoprazole sodium Form VI is identifiable by its PXRD pattern, a representative example of which is depicted in FIG. 4. Form VI is characterized by PXRD peaks at 17.9, 19.5, 20.4, 21.4, 24.6±0.2 degrees two-theta. Additional peaks occur at 6.3, 10.1, 15.5, 20.7, 23.0, 26.3, 29.4 and 29.9±0.2 degrees two-theta.

Pantoprazole sodium Form VI loses about 10-30% of its weight on heating to 150° C. A weight loss of 10-12% is considered the minimum weight loss to be expected for this form of pantoprazole sodium.

Pantoprazole sodium Form VI can be prepared by crystallizing pantoprazole sodium from a mixture of methanol and water. The following is a preferred procedure. Pantoprazole sodium is dissolved in a minimum amount of a methanol and water mixture, preferably about a 1:1 mixture. The solution is left exposed to the atmosphere allowing solvent to evaporate, while inducing slow crystallization of pantoprazole sodium. The mixture is conveniently left in an open flask overnight. The period of time needed for crystals of Form VI to form depends on the ratio of MeOH to water. More solvent must be evaporated, requiring more time, as the proportion of methanol is increased. A ratio of 1:1 methanol:water mixture is preferred because crystals usually form upon standing overnight.

Pantoprazole sodium Form VI also can be prepared by exposing pantoprazole sodium Form II to water vapors, preferably at room temperature, for a period of time sufficient to effect the conversion. The conversion of Form II into Form VI typically requires a period of 1-3 weeks at room temperature.

The Form VI crystals may be optionally dried gently at a temperature of up to 50° C., preferably 40° C. or less, for about 0-1 h, more preferably up to 30 min. More vigorous drying of Form VI samples at higher temperature and for longer periods of time, tends to result in a loss of crystallinity resulting in an amorphous material. Over-drying of Form VI crystals also may result in a mixture of Form I and amorphous form.

Pantoprazole Sodium Form VIII

Another aspect of this invention is a novel crystalline solid of pantoprazole sodium that can be obtained by contacting with methylethylketone ("MEK") under certain controlled conditions. This polymorph or pseudopolymorph has been denominated Form VIII.

Figure 5:
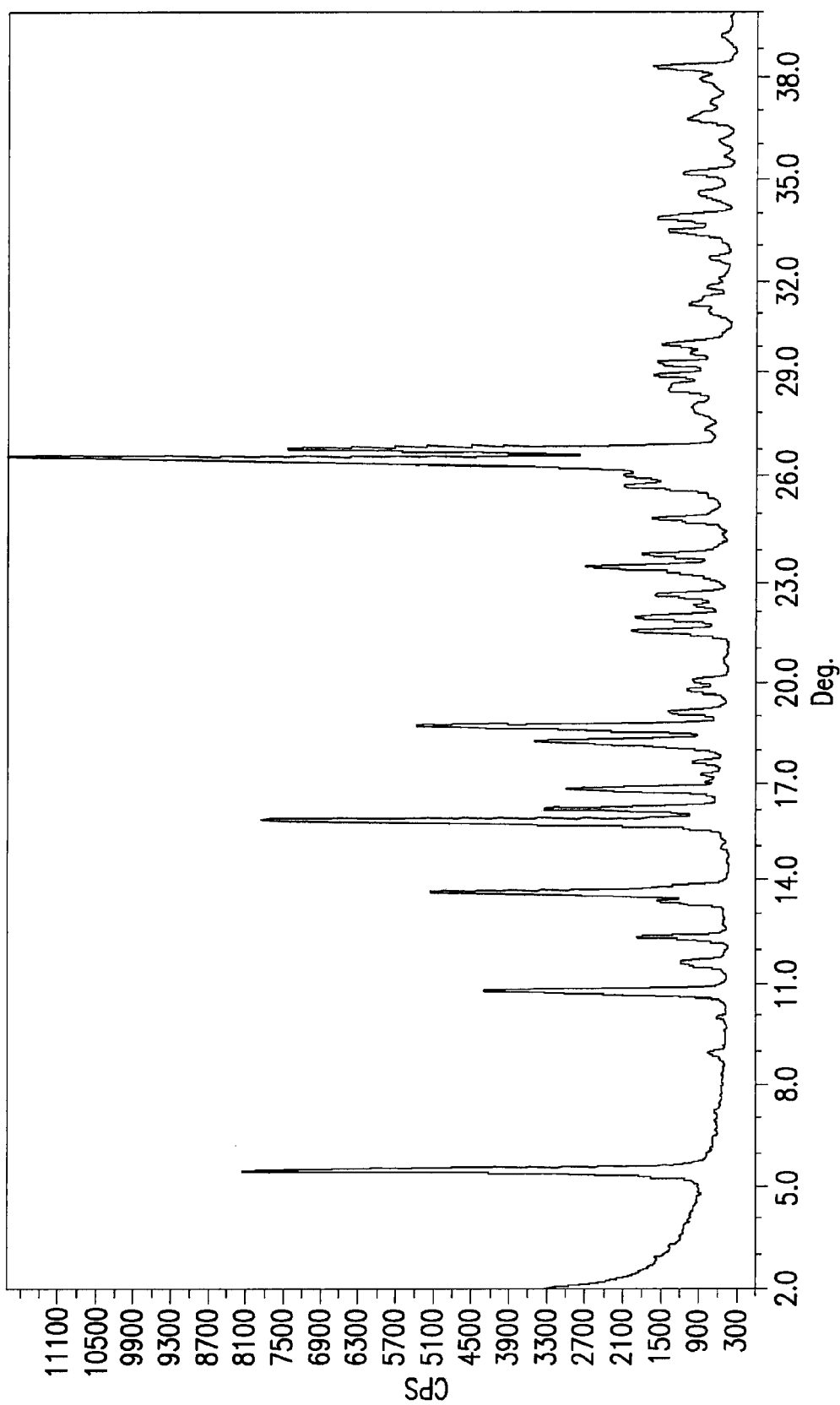
FIG. 5 is a representative PXRD pattern of pantoprazole sodium Form VIII.

Form VIII can be identified by its PXRD pattern, a representative example of which is provided in the diffractogram of FIG. 5. Form VIII is characterized by PXRD peaks at 5.6, 12.1, 13.0, 13.7±0.2 degrees two-theta. Additional peaks appear at 15.8, 16.1, 16.8, 17.1, 19.4, 20.0, 20.5, 22.6, 24.1, 24.5, 25.2, 25.5, 27.2±0.2 degrees two-theta.

Samples of Form VIII typically lose 16-18% of their weight upon heating to 125° C. Karl Fisher analysis shows that Form VIII contains 5-6 wt. % water.

Pantoprazole sodium Form VIII can be prepared by dissolving pantoprazole sodium Form II in MEK followed by crystallization without drying or by forming a heterogeneous mixture of pantoprazole sodium (in any solvation state or polymorphic form) and MEK and maintaining the mixture for a period of time sufficient to convert the crystals to Form VIII.

The obtained crystals may be optionally dried gently at a temperature of up to 50° C., more preferably up to 40° C., for about 0-1 h, more preferably up to 30 min. More vigorous drying of Form VIII at higher temperature or for a longer period of time, may cause a transformation into Form I monohydrate.

Pantoprazole Sodium Methylethylketone Solvate

Another aspect of this invention is crystalline pantoprazole sodium methylethylketone solvate.

Pantoprazole sodium Form VIII can be prepared by dissolving pantoprazole sodium Form II in MEK followed by crystallization without drying or by forming a heterogeneous mixture of pantoprazole sodium (in any solvation state or polymorphic form) and MEK and maintaining the mixture for a period of time sufficient to convert the crystals to Form VIII.

Pantoprazole Sodium Form IX

Another aspect of this invention is a novel crystalline solid of pantoprazole sodium that can be obtained by contacting with dimethylcarbonate under certain controlled conditions. This crystalline solid has been denominated Form IX.

Figure 6:
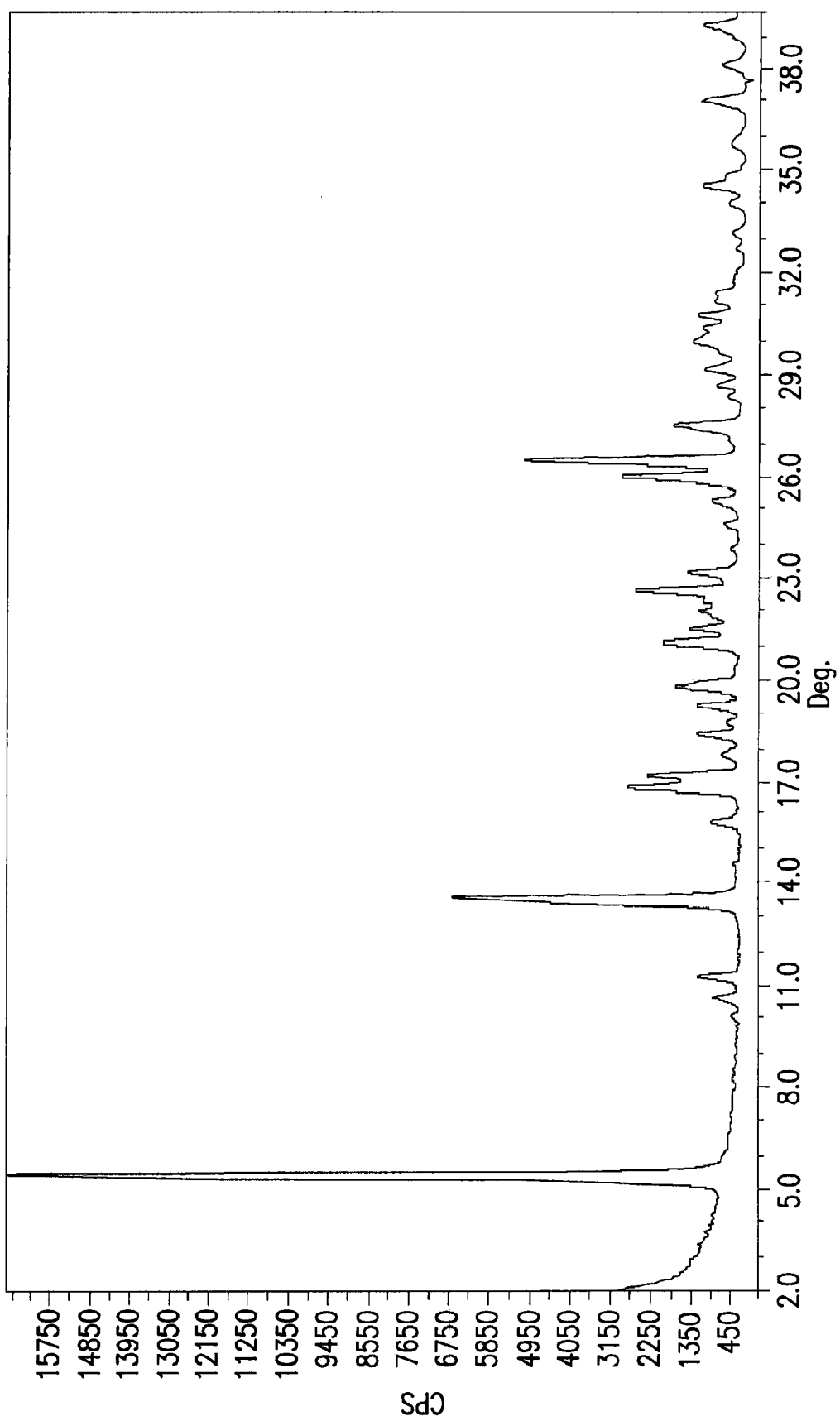
FIG. 6 is a representative PXRD pattern of pantoprazole sodium Form IX.

Pantoprazole sodium Form IX can be identified by its PXRD pattern, a representative example of which is provided in the diffractogram of FIG. 6. Form IX is characterized by PXRD peaks at 5.3, 13.6, 16.9, 17.3±0.2 degrees two-theta. Additional peaks appear at 10.6, 11.2, 18.5, 19.3, 19.9, 21.2, 22.8, 26.1, 26.7±0.2 degrees two-theta.

Typical samples of Form IX lose 14-20% of their weight on heating to 160° C. Karl Fisher analysis of Form IX shows that it contains about 9 wt. % water.

Form IX can be prepared by forming a heterogeneous mixture of pantoprazole sodium (in any solid state form) and dimethylcarbonate and maintaining the heterogeneous mixture for a period of time sufficient to effect conversion and separating the crystals from the dimethylcarbonate. At room temperature, complete conversion typically takes from 8 to 12 h.

The obtained crystals may be optionally dried gently at a temperature of up to 50° C., more preferably up to 40° C., for about 0-1 h, more preferably up to 30 min. More vigorous drying of Form IX sample at higher temperature or for a longer period of time may cause a transformation into Form I monohydrate.

Pantoprazole Sodium dimethylcarbonate Solvate

Another aspect of this invention is crystalline pantoprazole sodium dimethylcarbonate solvate.

The dimethylcarbonate solvate can be prepared by forming a heterogeneous mixture of pantoprazole sodium (in any solid state form) and dimethylcarbonate and maintaining the heterogeneous mixture for a period of time sufficient to effect conversion and separating the crystals from the dimethylcarbonate.

Pantoprazole Sodium Form X

Another aspect of this invention is a novel crystalline solid of pantoprazole sodium that can be obtained by contacting with 1-propanol under certain controlled conditions. This crystalline solid has been denominated Form X.

Figure 7:
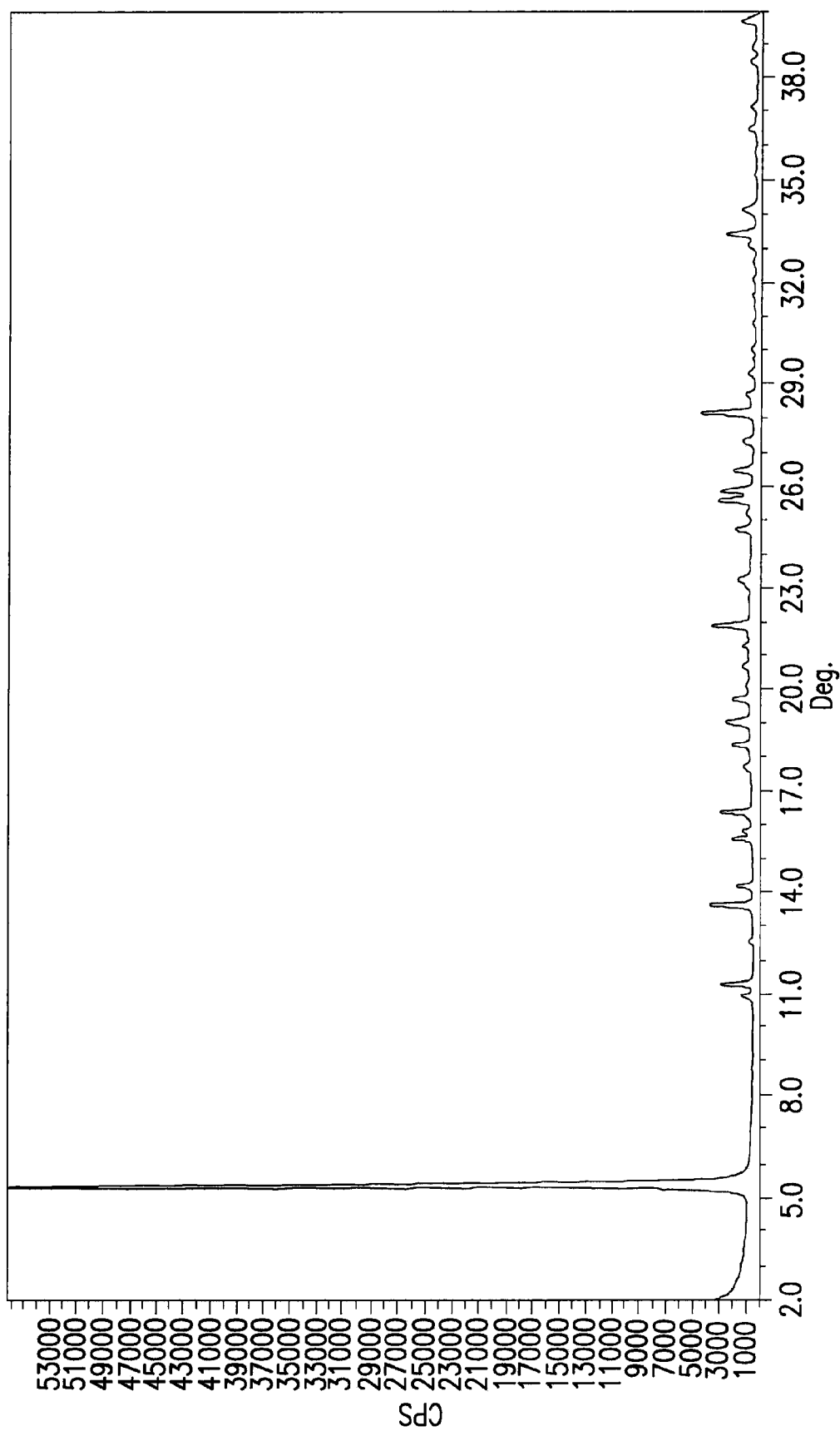
FIG. 7 is a representative PXRD pattern of pantoprazole sodium Form X.

Pantoprazole sodium Form X can be identified by its PXRD pattern, a representative example of which is provided in the diffractogram of FIG. 7. Form X is characterized by PXRD peaks at 16.4, 18.3, 19.0, 19.7, 21.9±0.2 degrees two-theta. Additional peaks appear at 10.9, 11.3, 13.6, 14.2, 15.5, 23.2, 24.7, 25.6, 25.8, 28.2±0.2 degrees two-theta.

Samples of Form X typically lose 11-13% of their weight on heating to 125° C., which corresponds to the expected 11.3% weight loss expected for a 1:1 solvate of 1-propanol and pantoprazole sodium. Karl Fisher analysis shows that Form X contains 5 to 7 wt. % water.

Due to the high solubility of pantoprazole sodium in 1-propanol, initial efforts at producing this form focused on crystallization processes. Again, conditions depleted of water, yet not rigorously anhydrous were investigated. We discovered that Form X can be obtained by crystallization from a solution formed by combining free pantoprazole with sodium hydroxide in 1-propanol.

The obtained crystals may be optionally dried gently at a temperature of up to 60 C, more preferably up to 40 C, for about 0-1 h, more preferably up to 30 min. More vigorous drying of Form X sample may cause to a transformation into Form I monohydrate.

Pantoprazole Sodium Propanol Solvate

Another aspect of this invention is crystalline pantoprazole sodium propanol solvate. We discovered that a propanol solvate can be obtained by crystallization from a solution formed by combining free pantoprazole with sodium hydroxide in 1-propanol.

Pantoprazole Sodium Form XI

Another aspect of this invention is a novel crystalline solid of pantoprazole sodium which has been denominated Form XI.

Figure 8:
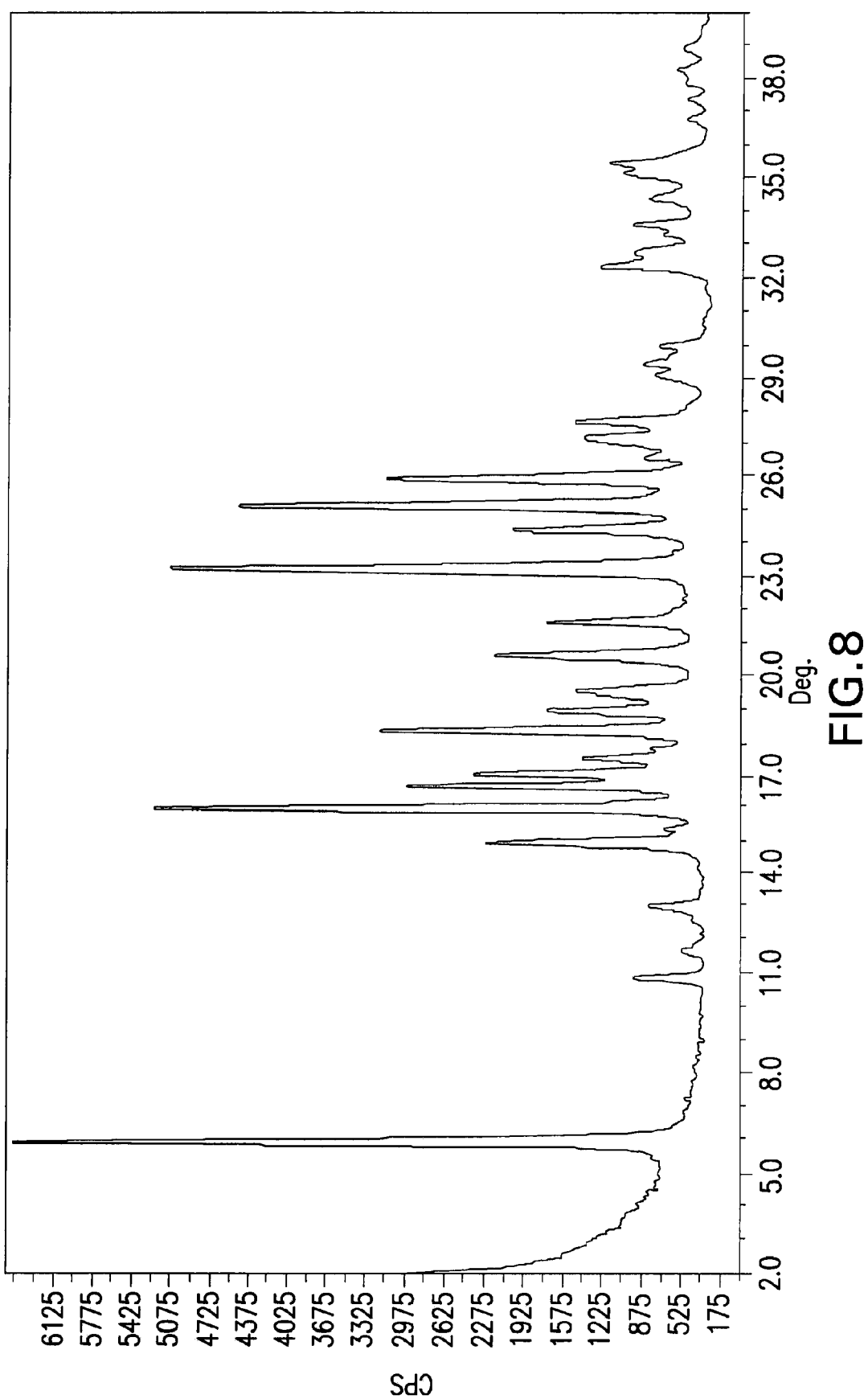
FIG. 8 is a representative PXRD pattern of pantoprazole sodium Form XI.

Form XI is identifiable by its PXRD pattern, a representative example of which is provided in the differactogram of FIG. 8. Form XI is characterized by PXRD peaks at 6.0, 16.0, 24.4, 25.1, 25.8±0.2 degrees two-theta. Additional peaks appear at 14.9, 16.7, 17.0, 18.2, 20.5, 21.6, 23.2±0.2 degrees two-theta. Form XI it loses less than 1% of its weight on heating up to 120° C., indicating that it is anhydrous.

Pantoprazole sodium Form XI may be prepared by forming a solution by contacting a hydrate of pantoprazole sodium with methanol, drying the solution with a drying agent, separating the drying agent and evaporating the methanol. In our experiments, the residue was not crystalline and we had difficulty crystallizing pantoprazole sodium from methanol and when successful we obtained a methanol solvate. The usually viscous oil residue can be converted to an anhydrous crystalline form of pantoprazole sodium by forming a heterogeneous mixture of the residue and acetone (the acetone should contain less than 0.01% water). Preferably from about 1:5 to about 2:5 acetone:residue (v/w) should be used. The heterogeneous mixture is agitated for a period of time for substantially all of the oily residue to become a crystalline solid. The conversion typically takes about 2-6 hours at room temperature.

Anhydrous Pantoprazole Sodium

Another aspect of this invention is crystalline anhydrous pantoprazole sodium. Anhydrous Pantoprazole sodium may be prepared by forming a solution by contacting a hydrate of pantoprazole sodium with methanol, drying the solution with a drying agent, separating the drying agent and evaporating the methanol. In our experiments, the residue was not crystalline and we had difficulty crystallizing pantoprazole sodium from methanol and when successful we obtained a methanol solvate. The usually viscous oil residue can be converted to an anhydrous crystalline form of pantoprazole sodium by forming a heterogeneous mixture of the residue and acetone (the acetone should contain less than 0.01% water). Preferably from about 1:5 to about 2:5 acetone:residue (v/w) should be used. The heterogeneous mixture is agitated for a period of time for substantially all of the oily residue to become a crystalline solid. The conversion typically takes about 2-6 hours at room temperature.

Pantoprazole Sodium Form XI

Another aspect of this invention is a novel crystalline solid of pantoprazole sodium that can be obtained by contacting with 2-methyl propanol under certain controlled conditions. This crystalline solid has been denominated Form XII.

Figure 9:
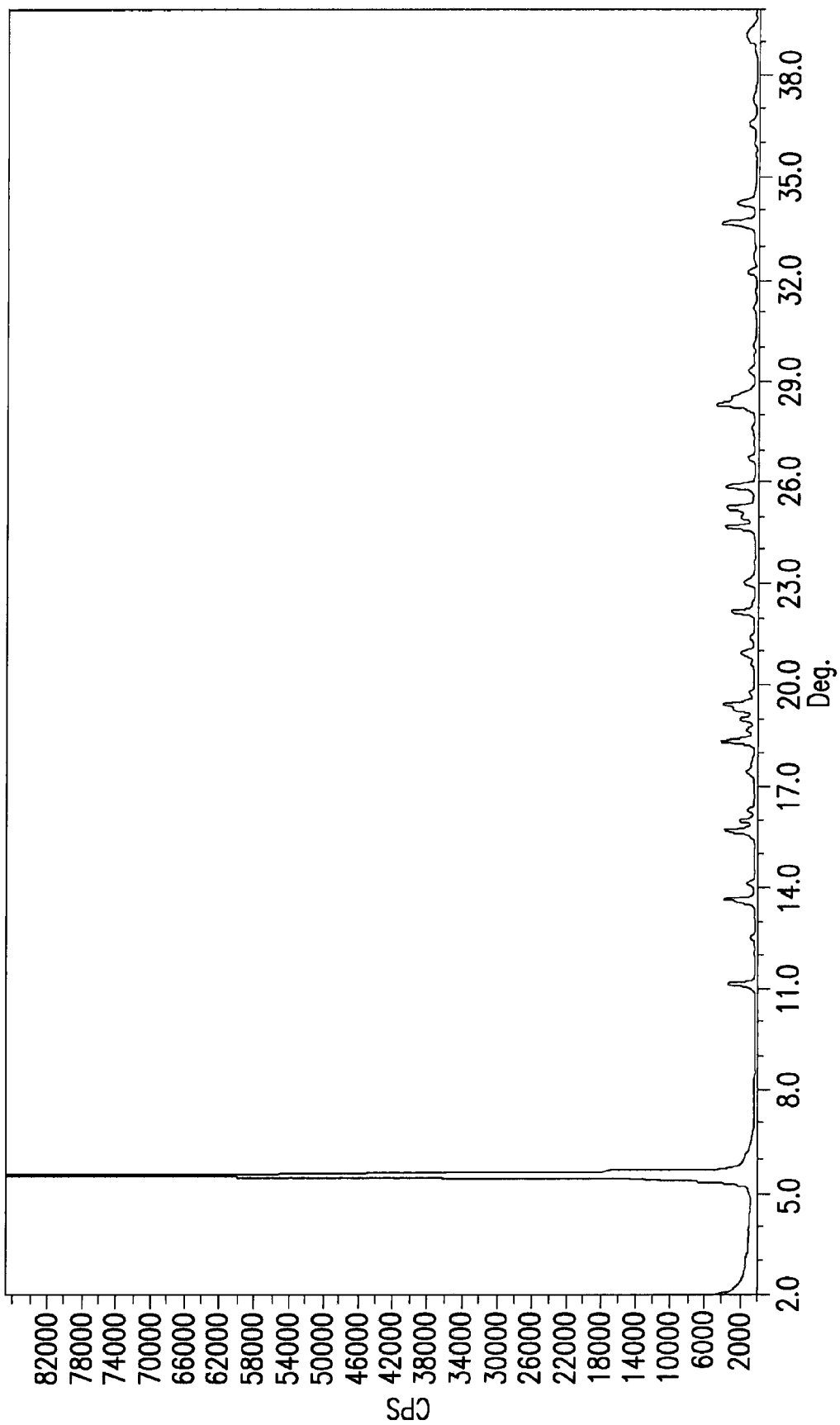
FIG. 9 is a representative PXRD pattern of pantoprazole sodium Form XII.

Form XII is identifiable by its PXRD pattern, a representative example of which is depicted in FIG. 9. Form XII is characterized by PXRD peaks at 5.6, 15.7, 19.4, 24.7, 28.3±0.2 degrees two-theta. Additional peaks appear at 11.1, 13.6, 16.0, 18.4, 19.4, 20.9, 22.2, 23.0, 25.3, 25.8±0.2 degrees two-theta.

Samples of Form XII lose about 15-20% of their weight on heating from 70 to 150° C. Karl Fisher analysis shows that Form XII contains 3-4 wt. % water Pantoprazole sodium Form XII can be prepared by forming a solution of pantoprazole sodium in 2-methyl propanol and then precipitating crystals of pantoprazole sodium from the solution. Preferably, the pantoprazole sodium is dissolved in a minimum amount of 2-methylpropanol at reflux temperature. Once a clear solution is obtained, heating may be ceased and crystals of pantoprazole sodium 2-methylpropanol solvate will precipitate from the solution if allowed to stand for a sufficient amount of time at room temperature, typically 10-20 h.

The obtained crystals may be optionally dried gently at a temperature of up to 60° C., more preferably up to 40° C., for about 0-1 h, more preferably for 30 min. or less. More vigorous drying at higher temperature or for a longer period of time, may cause the transformation of Form XII crystals into form XIII crystals. In some cases, more vigorous drying may result in a loss of crystallinity leading to amorphous material or mixtures of amorphous and crystalline material.

Pantoprazole Sodium 2-Methylpropanol Solvate

Another aspect of this invention is crystalline pantoprazole sodium 2-methylpropanol solvate. Pantoprazole sodium 2-methylpropanol solvate can be prepared by forming a solution of pantoprazole sodium in 2-methylpropanol and then precipitating crystals of pantoprazole sodium from the solution.

Pantoprazole Sodium Form XIII

Another aspect of this invention is a crystalline solid of pantoprazole sodium, which has been denominated form XIII. This for can also exist as a hydrate.

Figure 10:
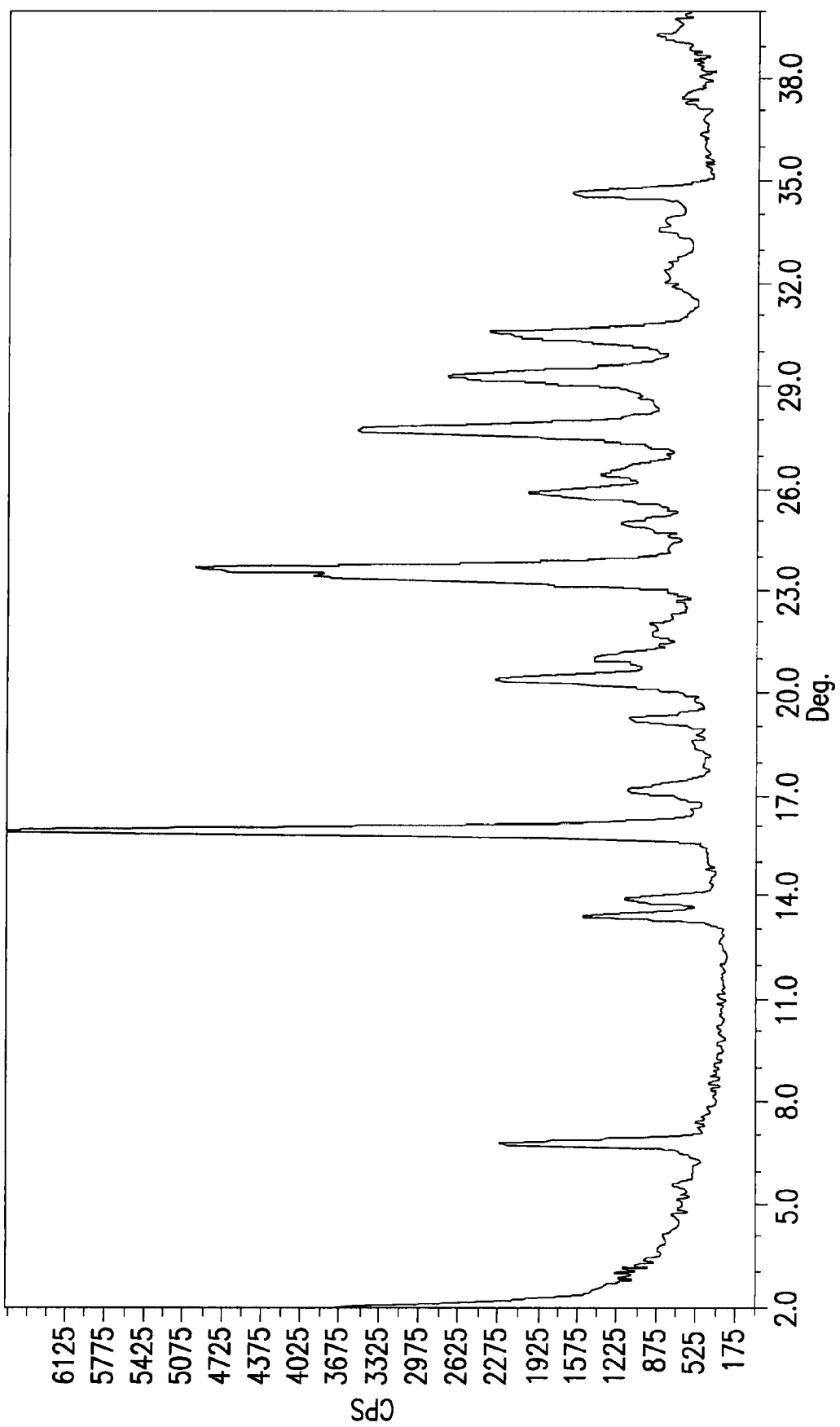
FIG. 10 is a representative PXRD pattern of pantoprazole sodium Form XIII.

Pantoprazole sodium Form XIII is identifiable by its PXRD pattern, a representative example of which is provided as FIG. 10. Form XIII is characterized by PXRD peaks at: 6.7, 15.9, 23.6, 27.7, 29.3, 30.6±0.2 degrees two-theta. Additional peaks appear at 13.4, 13.9, 17.1, 19.2, 20.4, 21.0, 25.9±0.2 degrees two-theta.

Samples of Form XIII lose from 7 to 10% upon heating to 150° C.

Pantoprazole sodium Form XIII can be prepared by forming a solution of pantoprazole sodium in a diluent selected from the group consisting of lower ketone solvents that are liquid at room temperature, such as acetone and methyl ethyl ketone ("MEK") and 2-propanol, crystallizing pantoprazole sodium Form XIII from the solution and separating the crystals from the diluent. Pantoprazole sodium is preferably dissolved in a minimum amount of the diluent at reflux temperature. Upon cessation of heating, crystals should begin to precipitate from a solution in acetone within about an hour, typically within about 15 minutes. When MEK is used, the mixture should be allowed to stand for 10-20 h because crystallization is slower.

Pantoprazole sodium Form XIII is also accessible by solid state thermal conversion. We have discovered that when pantoprazole sodium Form V is heated to temperatures above the recommended drying temperature for that solvate, the crystal structure will convert into the Form XIII crystal structure. Preferred conditions for conducting this conversion is heating to 50-80° C., more preferably 60-70° C., for from 1-5 h, more preferably 2-3 h.

Pantoprazole sodium Form XIII is also accessible by solid state thermal conversion of Form XII. The conditions for converting Form XII to Form XIII are generally similar to the conditions used when starting from Form V. In particular, Form XII is obtained by heating Form XII to 50-80° C., preferably 60-70° C. for 1-5 hours, preferably 2-3 hours. The obtained crystals may be optionally dried gently at a temperature of up to 60° C., more preferably up to 40° C., for about 0-1 h, more preferably 30 min. or less. More vigorous drying may cause a loss of crystallinity resulting in an amorphous material.

Pantoprazole Sodium Form XIV

Another aspect of this invention is a novel crystalline solid of pantoprazole sodium that can be obtained by contacting with 1-propanol under certain controlled conditions. This crystalline solid has been denominated Form XIV. This form can also exist as a hydrate.

Figure 11:
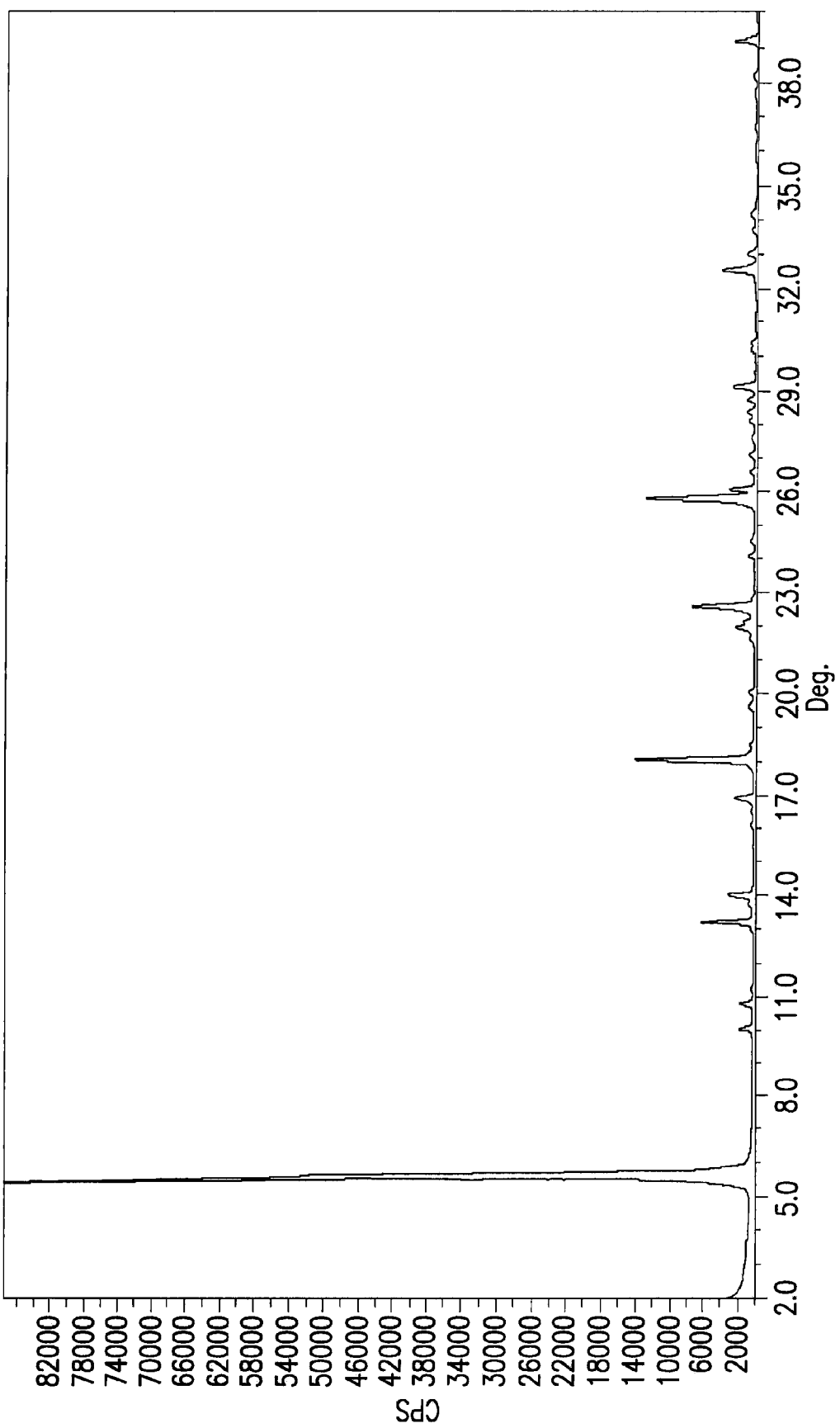
FIG. 11 is a representative PXRD pattern of pantoprazole sodium Form XIV.

Pantoprazole sodium Form XIV is identifiable by its PXRD pattern, a representative example of which is provided as FIG. 11. Form XIV is characterized by PXRD peaks at: 5.7, 17.0, 18.1, 22.7 and 25.8±0.2 degrees two-theta. Additional peaks appear at 10.2, 10.9, 13.3, 14.1 and 27.6±0.2 degrees two-theta.

Samples of Form XIV lose from 10-25% of their weight on heating to 170° C. Karl Fisher analysis shows that Form XIV contains between 2 and 6 wt. % water. Form XIV is therefore considered to contain 8-20 wt. % propanol.

Form XIV can be prepared by exposing pantoprazole sodium to vapors of 1-propanol. They may be contacted by maintaining the pantoprazole sodium under 1-propanol vapor for a period of time sufficient to convert the starting crystals to Form XIV. The solid:vapor phase conversion into Form XIV is slow and can take as much as a month to complete. Alternatively, Form XIV can be produced by forming a solution of pantoprazole sodium in 1-propanol, seeding the solution with Form XIV and precipitating dissolved pantoprazole from the solution as Form XIV. Crystallization typically takes 2-5 hours.

Pantoprazole Sodium Form XV

Another aspect of this invention is a novel crystalline solid of pantoprazole sodium that can be obtained by thermal conversion of pantoprazole sodium Form XIV. This crystalline solid has been denominated Form XV. This form can also exist as a hydrate.

Figure 12:
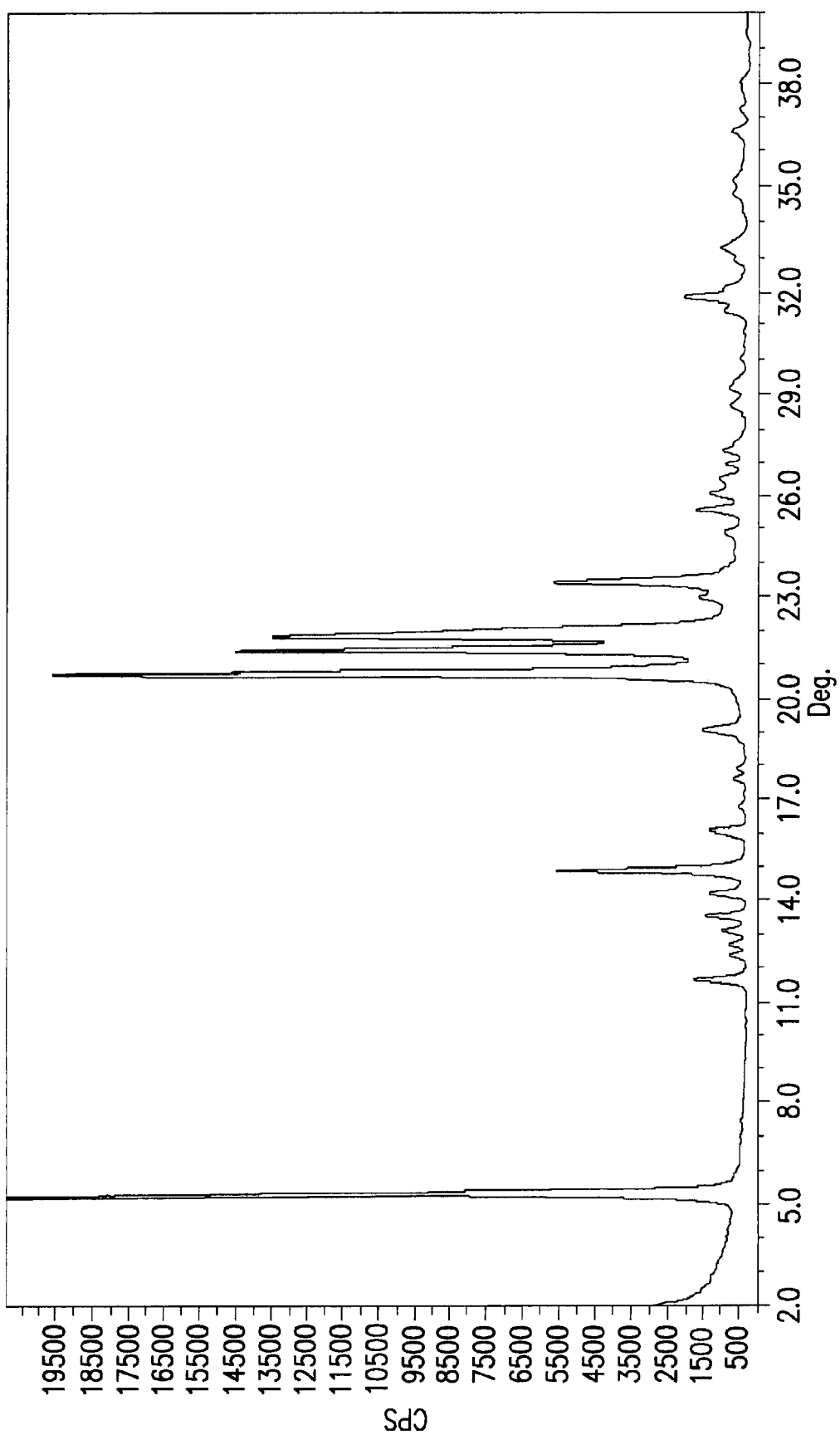
FIG. 12 is a representative PXRD pattern of pantoprazole sodium Form XV

Pantoprazole sodium Form XV is identifiable by its PXRD pattern, a representative example of which is provided as FIG. 12. Form XV is characterized by PXRD peaks at: 20.7, 21.4, 21.8 and 23.3±0.2 degrees two-theta. Additional peaks appear at 5.3, 11.6, 14.1, 14.8, 16.0 and 19.0±0.2 degrees two-theta. Karl Fisher analysis shows that Form XIV contains between 2 and 6 wt. % water.

Pantoprazole sodium Form XV can be produced from Form XIV. According to this procedure, Form XIV is heated to from 30 to 100° C. for a period of time sufficient to effect the conversion. Generally, Form XIV substantially completely converts to Form XV when kept overnight at about 40-60° C. The conversion may be conducted at ambient pressures at these temperatures. Conversion may be achievable at lower temperatures under reduced pressure. Progress of the conversion may be followed by monitoring the reduction in intensity of Form XIV characteristic peaks at 5.7, 7.0, 18.2, 22.7 and 25.8±0.2 degrees two theta in the PXRD pattern of Form XIV and the appearance and increase in the intensity of the peak at 20.7, 21.4, 21.8 and 23.3±0.2 degrees two-theta in the PXRD pattern of Form XV.

Pantoprazole Sodium Form XVI

Another aspect of this invention is a crystalline solid of pantoprazole sodium that can be obtained by contacting with toluene under certain controlled conditions. This crystalline solid has been denominated Form XVI. This form can also exist as a hydrate.

Figure 13:
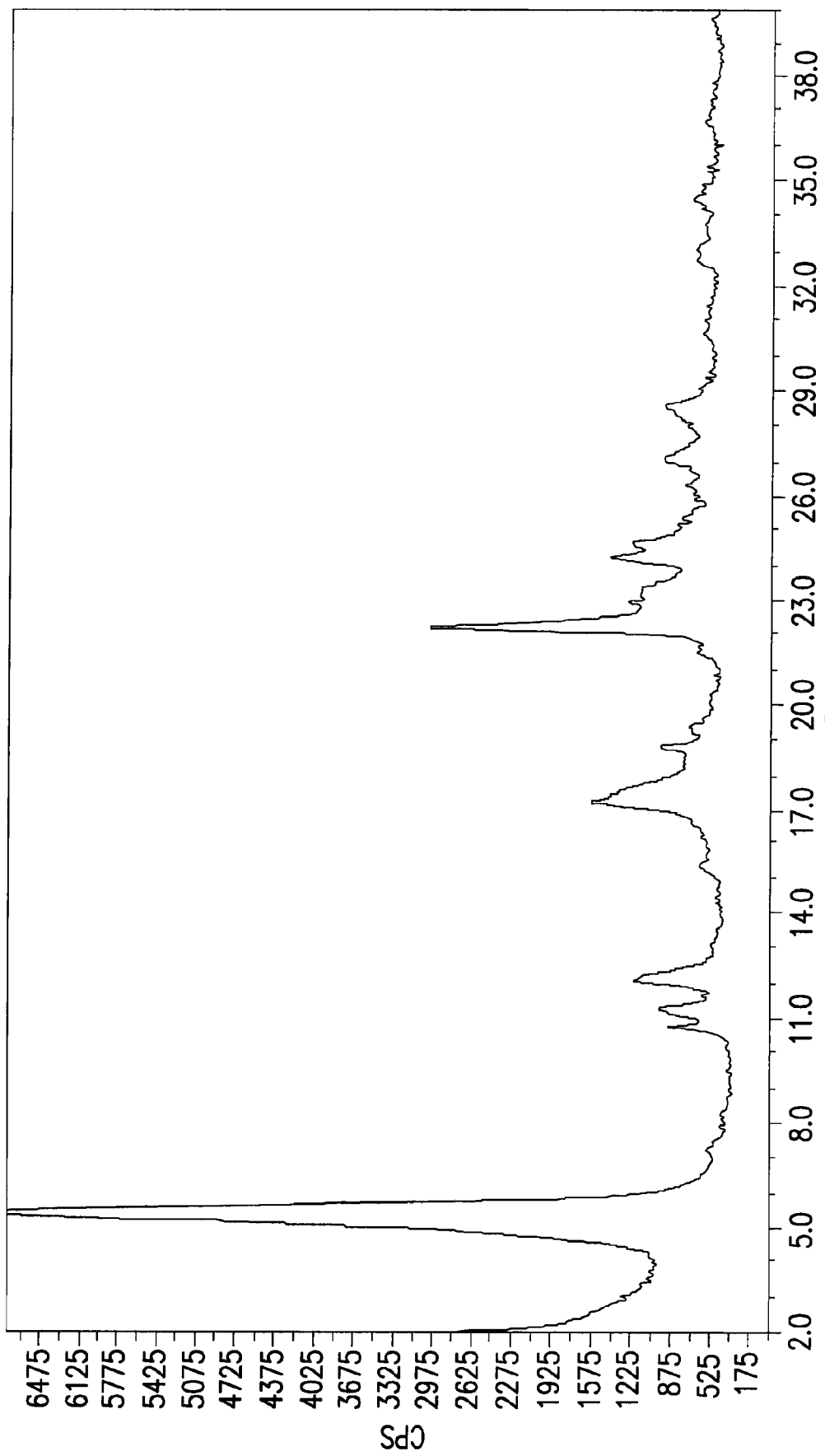
FIG. 13 is a representative PXRD pattern of pantoprazole sodium Form XVI.

Pantoprazole sodium Form XVI is identifiable by its PXRD pattern, a representative example of which is provided as FIG. 13. Form XVI is characterized by PXRD peaks at: 10.8, 11.4, 12.1 and 22.4±0.2 degrees two-theta. Additional peaks appear at 5.5, 17.4, 24.3, 24.8±0.2 degrees two-theta. Samples of Form XVI lose from 5-20% of their weight on heating to 170° C.

Pantoprazole sodium hydrate Form XVI can be produced by forming a solution of pantoprazole sodium in toluene diluent and precipitating crystals of pantoprazole sodium from the solution and separating the diluent. The procedure is further illustrated in Example 26.

Pantoprazole Sodium Form XVII

Another aspect of this invention is a novel crystalline solid of pantoprazole sodium which has been denominated Form XVII. Form XVII contains about 5-6 wt. % water according to Karl Fischer analysis and loses 18-22 wt. % of its mass upon heating from 25° C. to 160° C., indicating that it can contain from about 12 wt. % to about 17 wt. % methyl ethyl ketone.

Figure 14:
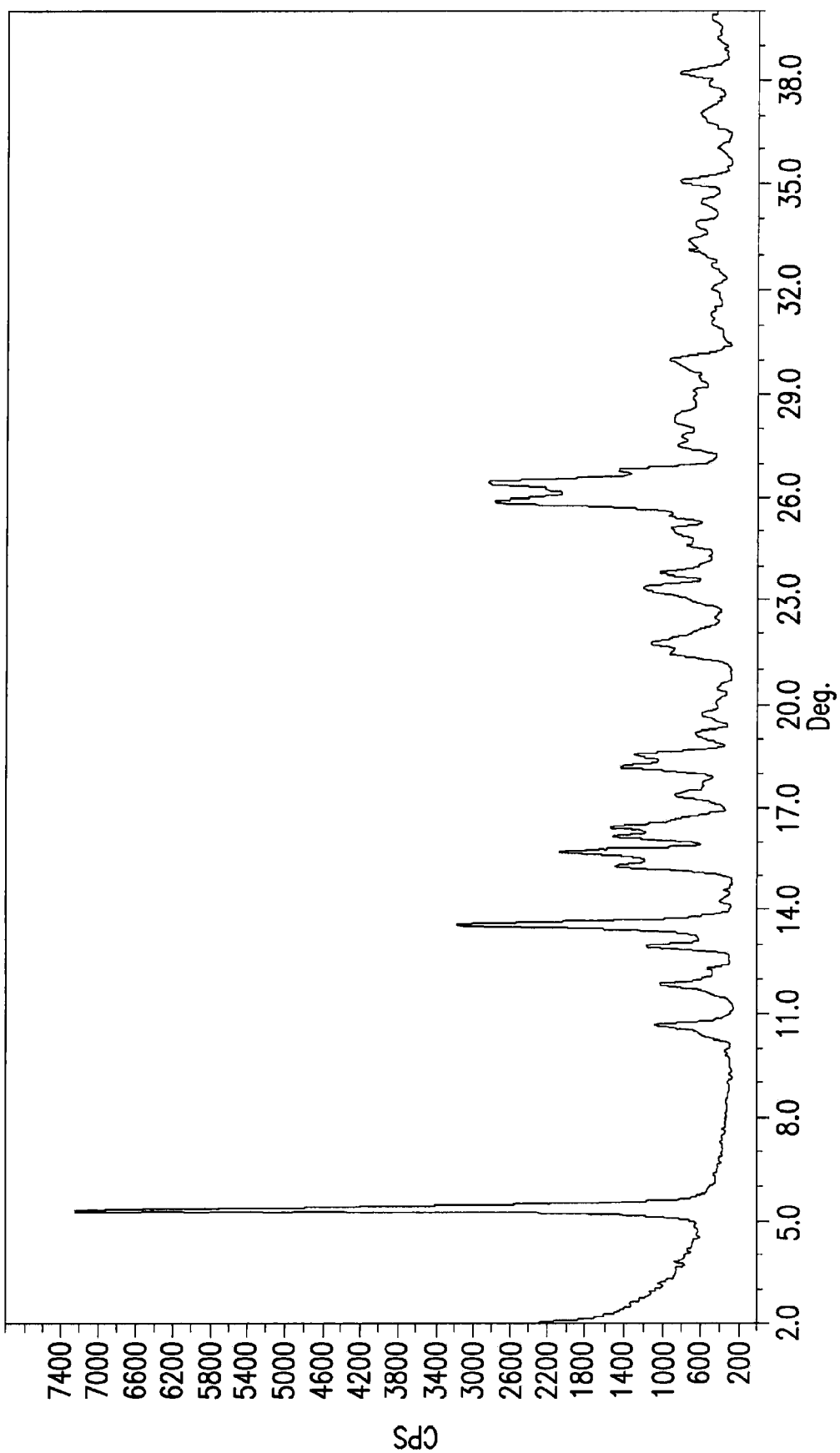
FIG. 14 is a representative PXRD pattern of pantoprazole sodium Form XVII.

Form XVII is identifiable by its PXRD pattern, a representative example of which is depicted in FIG. 14. Form XVII is characterized by a PXRD pattern having peaks at 15.2, 15.7, 25.8, and 26.5±0.2 degrees two-theta.

Pantoprazole sodium Form XVII can be prepared by forming and then sufficiently agitating a heterogeneous mixture of pantoprazole sodium (in any solid state form) in methyl ethyl ketone for a period of time sufficient to effect the conversion to Form XVII. The production of Form XVII after twenty four hours indicates that the heterogeneous mixture was sufficiently agitated to produce this crystalline form. However, the production of Form VIII is an indicator that the heterogeneous mixture was not sufficiently agitated and steps to increase the agitation, such as increasing a rate of stirring should be undertaken starting with new starting material. Such routine adjustment in the operating conditions is considered well within the ordinary skill in the art. Generally speaking, when working a typical laboratory scales of a few grams, mechanical or magnetic stirring of the heterogeneous mixture at 700 rpm or more should yield Form XVII. The temperature at which the heterogeneous mixture is maintained while being agitated is not critical to successful practice of the invention, though it has been convenient to work at temperatures in the range of 20-35° C., yet more preferably in the range of 25° C. to 30° C. A specific procedure for producing Form XVII is illustrated with Example 27, below.

Pantoprazole Sodium Hydrate-Methylethylketone Solvate

Another aspect of this invention is crystalline pantoprazole sodium hydrate-methylethylketone solvate. Pantoprazole sodium hydrate-methylethylketone solvate can be prepared by forming and then sufficiently agitating a heterogeneous mixture of pantoprazole sodium (in any solid state form) in methyl ethyl ketone for a period of time sufficient to effect the conversion to Form XVII.

Pantoprazole Sodium Form XVIII

Another aspect of this invention is a novel crystalline solid of pantoprazole sodium which has been denominated Form XVIII. It contains about 4-5 wt. % water according to Karl Fischer analysis and loses 10-11 wt. % of its mass upon heating from 25° C. to 160° C., indicating that it can contain from about 5 wt. % to about 7 wt. % acetone.

Figure 15:
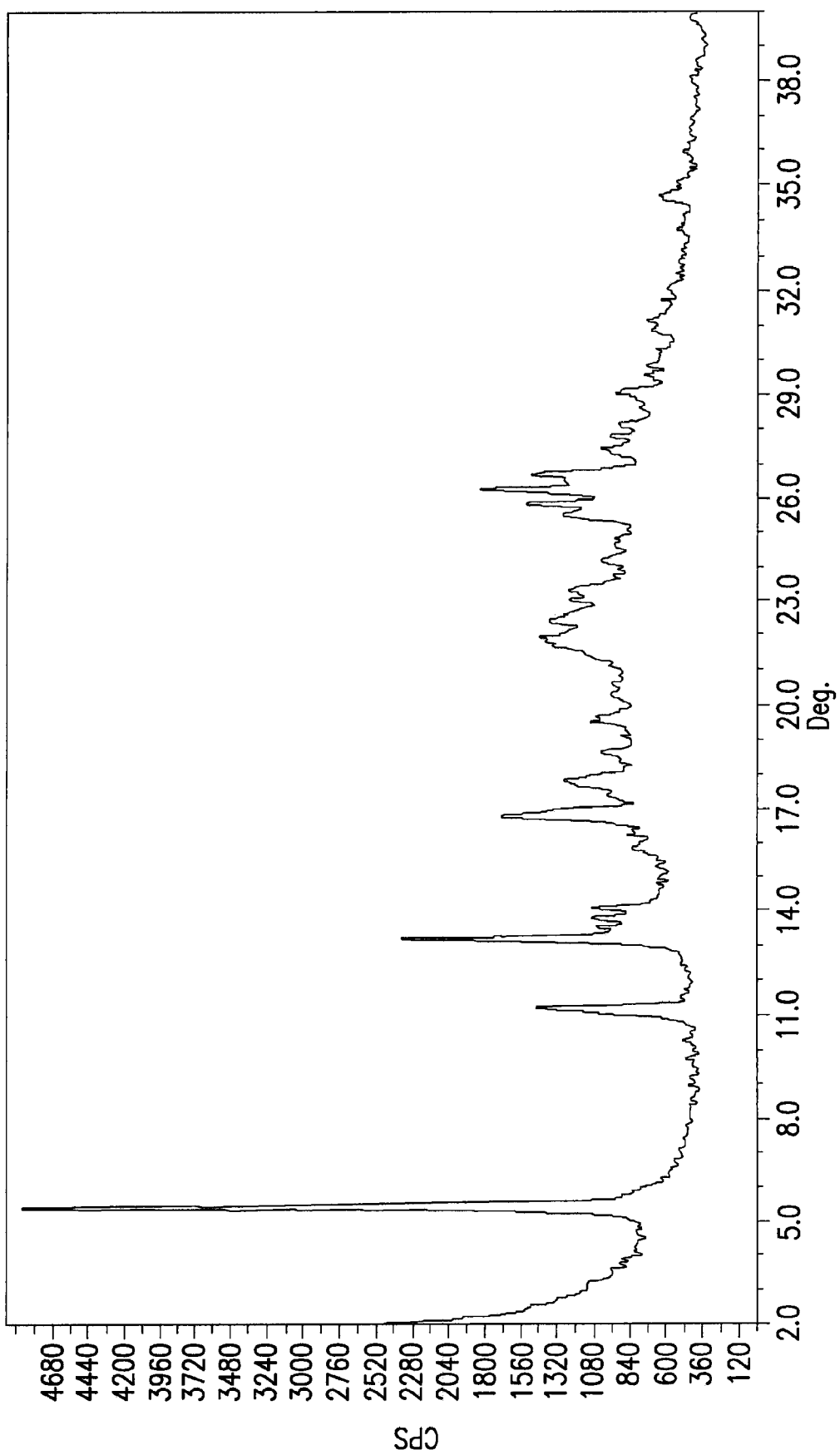
FIG. 15 is a representative PXRD pattern of pantoprazole sodium Form XVIII.

Form XVIII is identifiable by its PXRD pattern, a representative example of which is depicted in FIG. 15. Form XVIII is characterized by a PXRD pattern having peaks at 11.2, 13.2, 13.5, 13.8, 14.1±0.2 degrees two-theta.

Pantoprazole sodium Form XVIII can be prepared by forming a heterogeneous mixture of pantoprazole sodium (in any solid state form) in acetone and then separating the acetone from the crystals. The conversion takes from about 15 minutes to about 2 hours at room temperature. An illustrative procedure for preparing Form XVIII is provided in Example 28 below.

Pantoprazole Sodium Hydrate-Acetone Solvate

Another aspect of this invention is crystalline pantoprazole sodium hydrate-acetone solvate. Pantoprazole sodium hydrate-acetone solvate can be prepared by forming a heterogeneous mixture of pantoprazole sodium (in any solid state form) in acetone and then separating the acetone from the crystals.

Pantoprazole Sodium Form XIX

Another aspect of this invention is a novel crystalline solid of pantoprazole sodium which has been denominated Form XIX. It contains about 6-9 wt. % water according to Karl Fischer analysis and loses the same amount of its mass upon heating from 25° C. to 170° C., indicating that it contains little of any other solvent within its crystal structure.

Figure 16:
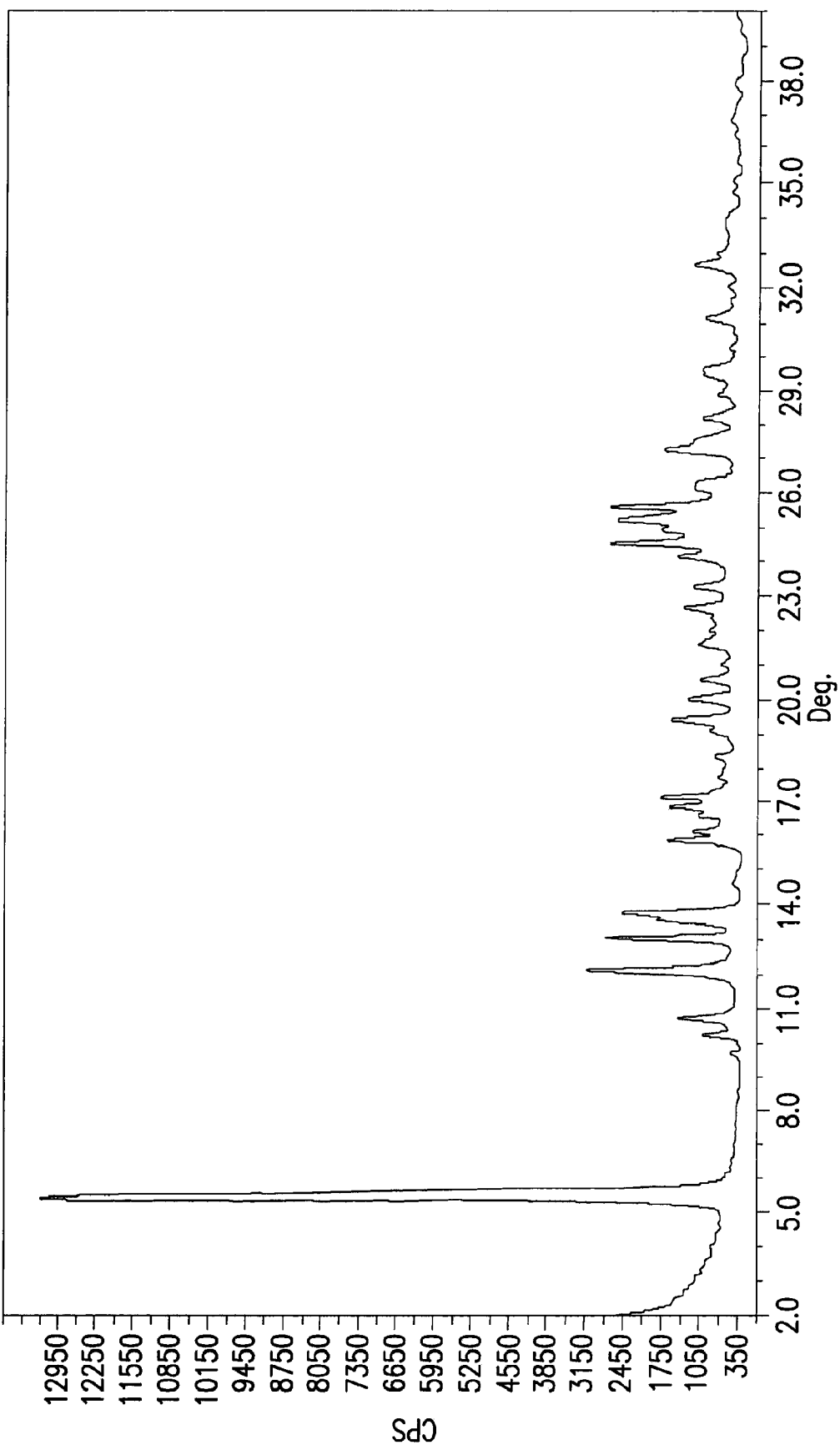
FIG. 16 is a representative PXRD pattern of pantoprazole sodium Form XIX.

Form XIX is identifiable by its PXRD pattern, a representative example of which is depicted in FIG. 16. Form XIX is characterized by a PXRD pattern having peaks at 11.3, 13.4, 13.8, 26.2 and 26.6±0.2 degrees two-theta.

Pantoprazole sodium Form XIX can be prepared by forming a homogeneous mixture of pantoprazole sodium (in any solid state form) in water under ambient, elevated or vacuum conditions and then drying the residue. Preferred drying conditions 50° C. at ambient pressure.

Pantoprazole Sodium Dihydrate

Another aspect of this invention is pantoprazole sodium dihydrate. Pantoprazole sodium dihydrate can be prepared by forming a homogeneous mixture of pantoprazole sodium (in any solid state form) in water under ambient, elevated or vacuum conditions and then drying the residue.

Pantoprazole Sodium Form XX

Another aspect of this invention is a novel crystalline solid of pantoprazole sodium which has been denominated Form XX. It contains about 11-12 wt. % water according to Karl Fischer analysis.

Figure 17:
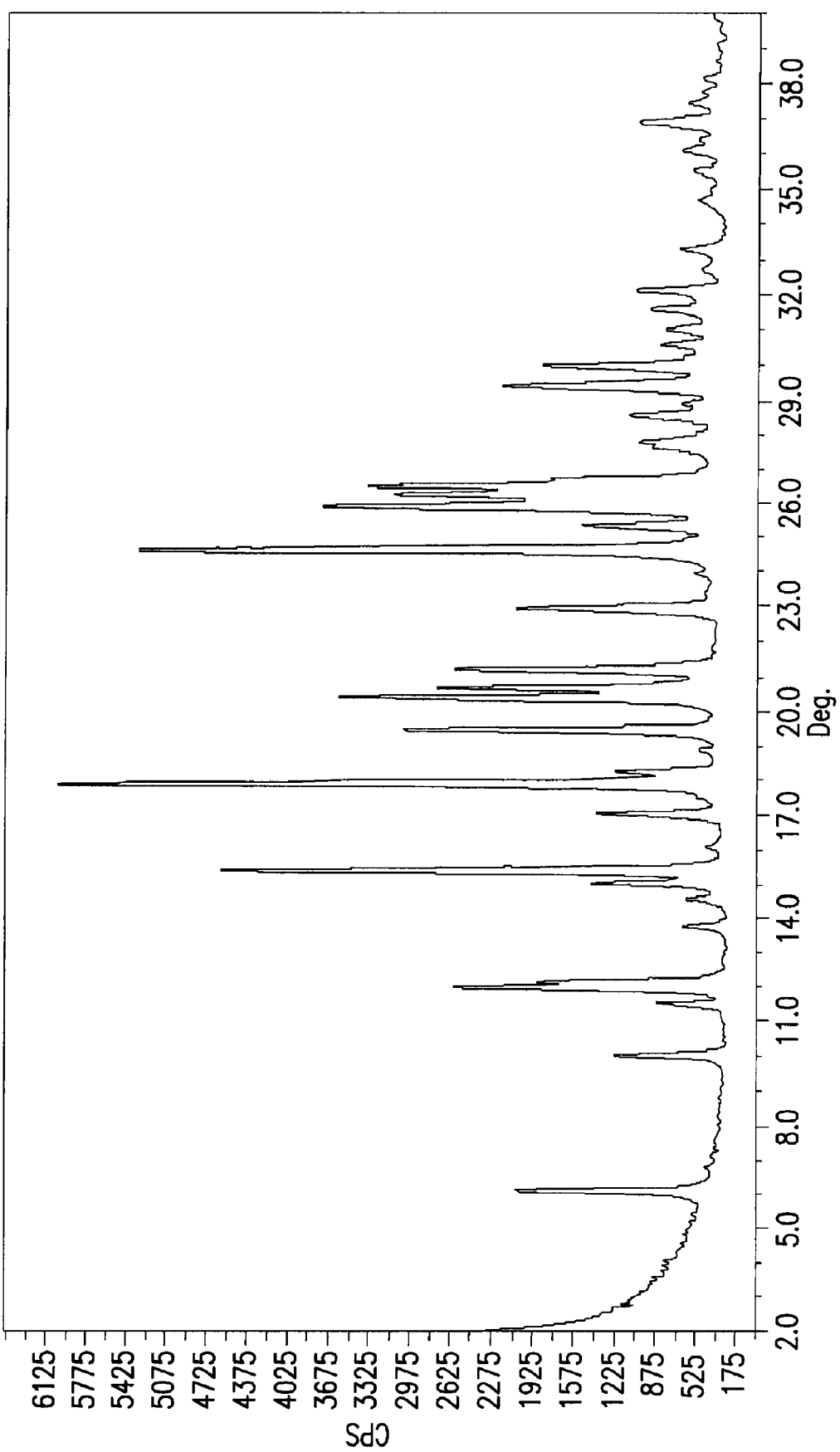
FIG. 17 is a representative PXRD pattern of pantoprazole sodium Form XX.

Form XX is identifiable by its PXRD pattern, a representative example of which is depicted in FIG. 17. Form XX is characterized by a PXRD pattern having peaks at 15.4, 17.9, 24.6, 25.9, 26.2, and 26.5±0.2 degrees two-theta.

Pantoprazole sodium Form XX can be prepared by forming a heterogeneous mixture of pantoprazole sodium (in any solid state form) in moist hydrocarbons. The hydrocarbon component of the liquid phase of the mixture is selected from any liquid aromatic hydrocarbon or any liquid aliphatic hydrocarbon in which water is soluble is soluble to the extent of at least one percent. There may be mentioned from among the suitable aromatic hydrocarbons, toluene, o-, —and p-xylenes and mixtures thereof as well as other alkyl substituted benzenes having substituents of 1-6 aliphatic carbon atoms. Preferred aliphatic hydrocarbons contain from five to twelve carbon atoms, with reagent grade mixtures of hexanes, n-hexane and n-heptane being most preferred.

In accordance with the process for preparing pantoprazole sodium Form XX, the hydrocarbon component of the liquid phase is contacted with at least enough water to produce a liquid phase containing from about 1 wt. % to about 10 wt. % water, more preferably about 1 wt. % to about 5 wt. % water. Depending upon the hydrocarbon, excess water may be used so that saturation of the hydrocarbon results in the formation of a 1-10 wt. % mixture. Excess water can then be separated by from the liquid phase by conventional means such as a separatory funnel.

The starting pantoprazole sodium is contacted with the liquid phase to form a heterogeneous mixture that is maintained under conditions effective to convert it into Form XX. Stirring the mixture at room temperature for about 5 days is generally sufficient to complete the conversion.

After separating the liquid phase from the crystals, Form XX can be dried under mild conditions such as 50° C. at 10 mm Hg vacuum without causing significant dehydration.

Illustrative procedures for preparing pantoprazole sodium Form XX are provided in Examples 30-33, below.

Pantoprazole Sodium Trihydrate

Another aspect of this invention is crystalline pantoprazole sodium trihydrate. Pantoprazole sodium trihydrate can be prepared by forming a heterogeneous mixture of pantoprazole sodium (in any solid state form) in moist hydrocarbons. The hydrocarbon component of the liquid phase of the mixture is selected from any liquid aromatic hydrocarbon or any liquid aliphatic hydrocarbon in which water is soluble is soluble to the extent of at least one percent. There may be mentioned from among the suitable aromatic hydrocarbons, toluene, o-, C and p-xylenes and mixtures thereof as well as other alkyl substituted benzenes having substituents of 1-6 aliphatic carbon atoms.

For convenience, the characteristic PXRD peaks of the novel crystalline polymorphs and solvates of the present invention are set forth in Table 1.

TABLE I

| Crystal Form | Unique PXRD Peak Combinations (degrees two-theta) |
|---|---|
| II | 16.6, 16.9, 17., 21.3, 21.7 22.2 |
| IV | 5.5, 13.8, 16.5, 17.0, 26.2, 26.6 |
| V | 5.8, 12.3, 19.2, 19.7, 20.3, 20.7 |
| VI | 17.9, 19.5, 20.4, 21.4, 24.6 |
| VIII | 5.6, 12.1, 13.0, 13.7 |
| IX | 5.3, 13.6, 16.9, 17.3 |
| X | 16.4, 18.3, 19.0, 19.7, 21.9 |
| XI | 6.0, 16.0, 24.4, 25.1, 25.8 |
| XII | 5.6, 15.7, 19.4, 24.7, 28.3 |
| XIII | 6.7, 15.9, 23.6, 27.7, 29.3, 30.6 |
| XIV | 5.7, 17.0, 18.1, 22.7, 25.8 |
| XV | 20.7, 21.4, 21.8, 23.3 |
| XVI | 10.8, 11.4, 12.1, 22.4 |
| XVII | 15.2, 15.7, 25.8, 26.5 |
| XVIII | 11.2, 13.2, 13.5, 13.8, 14.1 |
| XIX | 11.3, 13.4, 13.8, 26.2, 26.6 |
| XX | 15.4, 17.9, 24.6, 25.9, 26.2, 26.5 |

Amorphous Pantoprazole Sodium

Figure 18:
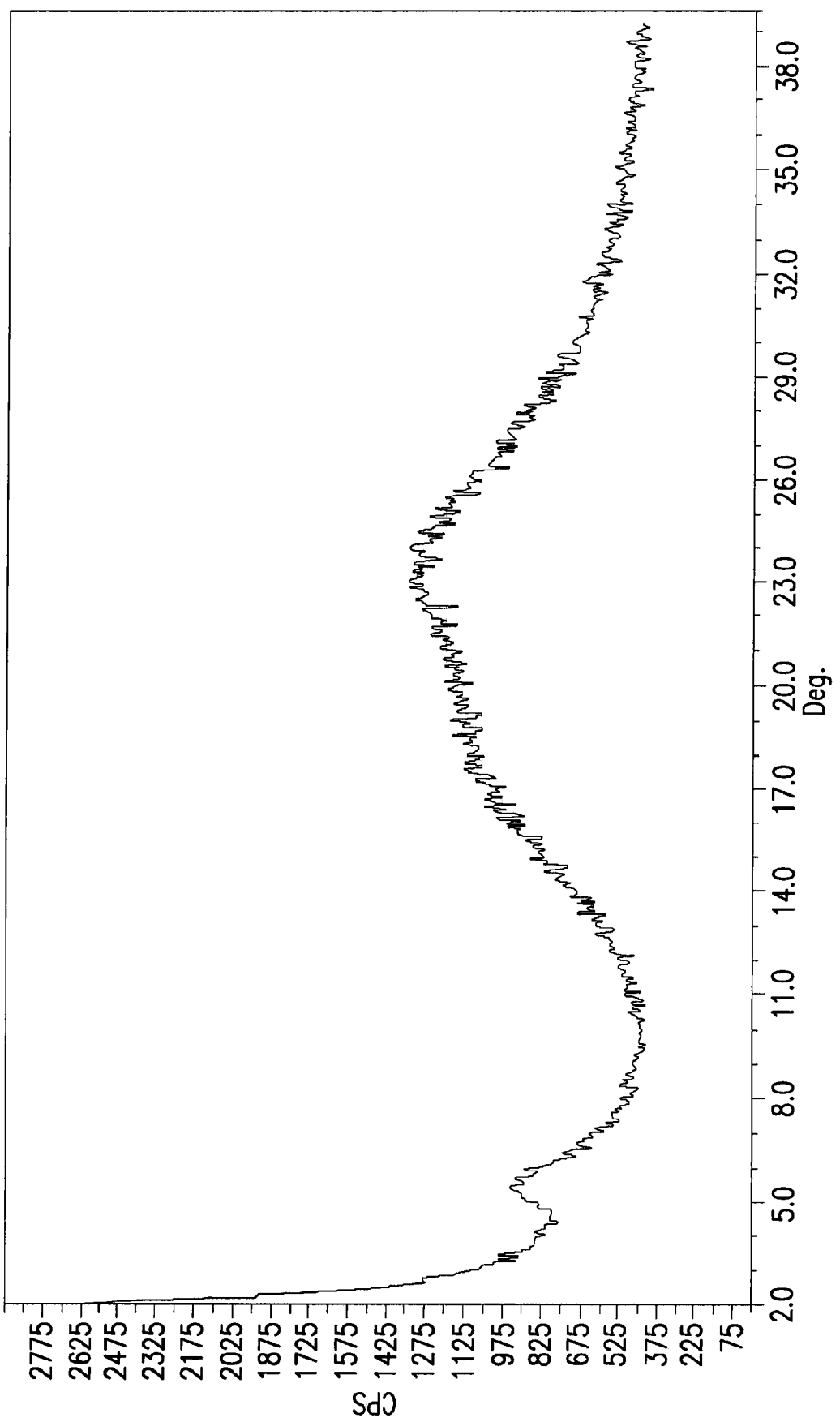
FIG. 18 is a representative PXRD pattern of amorphous pantoprazole sodium.

Another aspect of this invention is novel amorphous pantoprazole sodium, which produces a featureless PXRD pattern, as shown in FIG. 18.

Various processes that can be used to prepare amorphous pantoprazole sodium have already been mentioned in this disclosure. It may be prepared by excessive heating of pantoprazole sodium Forms V and XII, which leads to amorphous material via the intermediate polymorph Form XIII. When starting with Form XIII, preferred heating conditions are from 50 to 80° C., more preferably from 60 to 70° C. Complete destruction of crystallinity is usually complete in 2-5 h under these conditions. Heating pantoprazole sodium Form VI under these conditions also yields amorphous material.

Amorphous pantoprazole sodium also is accessible by dissolving crystalline pantoprazole sodium or any solvate thereof in a $C_1$-$C_4$ lower alcohol, then evaporating the alcohol to leave a semi-solid or liquid residue, forming a heterogeneous mixture of the residue and any solvent in which pantoprazole sodium is not appreciably soluble and maintaining the heterogeneous mixture until the residue solidifies, which typically takes 1 to 3 hours at room temperature.

Amorphous pantoprazole sodium also is accessible by precipitation of pantoprazole sodium from a solution of pantoprazole sodium in acetonitrile. Preferably, the pantoprazole sodium is dissolved in a minimum amount of acetonitrile and precipitation is induced by adding any liquid in which pantoprazole sodium is not appreciably soluble. Precipitation is usually complete within about 24 hours.

Amorphous pantoprazole sodium also is accessible by precipitation from a solution in toluene. The solution is prepared by dissolving pantoprazole free base and sodium hydroxide in the toluene. The sodium hydroxide is preferably added to the toluene as a concentrated aqueous solution, most preferably about a 47% aqueous solution. After precipitation, the amorphous pantoprazole precipitate is separated from the toluene after which it may be conventionally dried. Suitable drying conditions include 45° C. under 10 mm Hg vacuum.

Amorphous pantoprazole sodium also can be prepared by heating any form of pantoprazole sesquihydrate to 100° C. or higher temperature.

We have also discovered new processes for preparing known pantoprazole sodium hydrates.

Processes for Preparing Pantoprazole Sodium Monohydrate

Pantoprazole sodium monohydrate may be prepared by forming a solution of pantoprazole and sodium hydroxide in a diluent selected from the group consisting of tetrahydrofuran, methanol, 2-propanol, butanol, dimethylcarbonate, acetone, acetonitrile, and 1-propanol, precipitating crystals of pantoprazole sodium monohydrate from the solution, and separating the crystals from the diluent. The starting material may be pantoprazole sodium or any solvate of it. Alternatively, the solution may be formed by separately adding free pantoprazole and sodium hydroxide. Sodium hydroxide may be conveniently added separately as a solid or aqueous sodium hydroxide. Regardless of the method by which pantoprazole and sodium hydroxide are contacted with the diluent, the amounts of starting material and diluent used are preferably such as to yield a concentration corresponding to about 0.2 to 1 g of pantoprazole sodium per milliliter of diluent.

Depending upon the concentration and choice of diluent, it may be necessary to heat the mixture to reflux to obtain a clear solution. When the solution is refluxed, crystallization may be induced by cessation of heating and allowing the mixture to return to room temperature. Crystallization may also be induced by adding an anti-solvent to the mixture. Preferred anti-solvents are MTBE, toluene and cyclohexane. Particularly preferred diluent/anti-solvent combinations are further illustrated with Examples.

Pantoprazole sodium monohydrate may be prepared by forming a heterogeneous mixture by contacting pantoprazole sodium and a diluent selected from the group consisting of dimethylcarbonate and acetone, and recovering pantoprazole sodium monohydrate Form I from the heterogeneous mixture. Preferred starting materials for the heterogeneous process are pantoprazole sodium monohydrate Form II, amorphous pantoprazole sodium and pantoprazole sodium sesquihydrate.

Processes for Preparing Known Pantoprazole Sodium Sesquihydrate

Pantoprazole sodium Sesquihydrate can be prepared by forming a solution of pantoprazole and sodium hydroxide in a diluent selected from the group consisting of 2-propanol, tetrahydrofuran, acetonitrile, methanol, ethanol, water, mixtures of sec-butanol and dichloromethane, and ethyl acetate, precipitating crystals of pantoprazole sodium sesquihydrate from the solution, and separating the crystals from the diluent. The starting material may be pantoprazole sodium or any solvate of it. Alternatively, the solution may be formed by separately adding free pantoprazole and sodium hydroxide. Sodium hydroxide may be conveniently added separately as solid or aqueous sodium hydroxide. Regardless of the method by which pantoprazole and sodium hydroxide are contacted with the diluent, the amounts of starting material and diluent used are preferably such as to yield a concentration corresponding to about 0.5 to 1 g of pantoprazole sodium per milliliter of diluent.

Depending upon the concentration and choice of diluent, it may be necessary to heat the mixture to reflux to obtain a clear solution. When the solution is refluxed, crystallization may be induced by cessation of heating and allowing the mixture to return to room temperature. Crystallization may also be induced by adding an anti-solvent to the mixture. Preferred anti-solvents are MTBE and heptane.

When the diluent is methanol or ethanol, the starting materials are preferably free pantoprazole and solid sodium hydroxide.

Pantoprazole sodium sesquihydrate also can be prepared by forming a heterogeneous mixture by contacting pantoprazole sodium and a diluent selected from the group consisting of ethyl acetate, dichloromethane, water, dimethylcarbonate and 2-propanol, and recovering pantoprazole sodium sesquihydrate from the heterogeneous mixture. The amount of pantoprazole used is preferably from about 0.1 g to 1 g per milliliter of diluent. Preferably, the diluents water and mixtures of water and 2-propanol are used in a minor amount relative to the pantoprazole sodium on a weight basis. When the diluent is ethyl acetate, dichloromethane or dimethylcarbonate, it is preferably added in an amount equal or greater amount than the amount of pantoprazole sodium on a weight basis Compositions and Dosage Forms of Crystalline And Amorphous Pantoprazole Sodium Pantoprazole sodium Forms II, IV, V, VI, VIII, IX, X, XI, XII, XIII, XIV, XV, XVI, XVII, XVIII, XIX, XX and amorphous pantoprazole sodium are useful as the active ingredient in pharmaceutical compositions and dosage forms intended for administration of the gastric acid secretion inhibitor pantoprazole. Accordingly, these novel solid forms are useful for treating erosive esophagitis associated with GERD.

Pharmaceutical compositions of the present invention contain pantoprazole sodium Form II, IV, V, VI, VIII, IX, X, XI, XII, XIII, XIV, XV, XVI, XVII, XVIII, XIX or XX, amorphous pantoprazole sodium or mixtures thereof with each other or with other forms of pantoprazole sodium. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include for example alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate.

When a dosage form such as a tablet is made by compaction of a powdered composition, the composition is subjected to pressure from punches and a die. Some excipients and active ingredients have a tendency to adhere to the surfaces of the punches and die, which can cause the product to have pitting and other surface irregularities. A lubricant can be added to the composition to reduce adhesion and ease release of the product form the die. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, pantoprazole sodium Forms II, IV, V, VI, VIII, IX, X, XI, XII, XIII, XIV, XV, XVI, XVII, XVIII, XIX or XX, amorphous pantoprazole sodium or mixtures thereof are suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

A dosage form of the present invention is a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms preferably contain a dosage level of about 10 to about 100 mg of pantoprazole sodium Form I II, IV, V, VI, VIII, IX, X, XI, XII, XIII, XIV, XV, XVI, XVII, XVIII, XIX or XX, amorphous pantoprazole sodium or mixtures thereof, more preferably about 45 mg. Other dosages may also be administered depending on the need.

Having thus described the present invention with reference to certain preferred embodiments, the invention will be further illustrated by the examples which follow. These examples are provided for illustrative purposes only and are not intended to limit the scope of the invention in any way.

EXAMPLES

Pantoprazole and pantoprazole sodium were obtained from commercial sources. All organic solvents and reagents were used as received from commercial sources.

Preparation of Pantoprazole Sodium Form II

Example 1

A 100 ml round bottomed flask equipped with a magnetic stir bar was charged with acetone (50 ml). Pantoprazole (10 g, 25.7 mmol) was then added to the flask. After the pantoprazole had completely dissolved, the solution was cooled to about 2° C. Forty seven percent sodium hydroxide (aq.) equivalent to 2.4 grams of solid sodium hydroxide (60.0 mmol) was slowly added to the cooled solution. A precipitate began to form immediately. The mixture was stirred for another two hours while the flask was allowed to warm to room temperature. The precipitate was filtered and washed with acetone (20 ml) and dried at 40° C. under vacuum to yield pantoprazole sodium Form II (6.9 g, 65%).

Preparation of Amorphous Pantoprazole Sodium

Example 2

Pantoprazole sodium Form II (5.0 g) was dissolved at room temperature in absolute ethanol (120 ml) in a flask equipped with a Soxlet extractor containing 30 g of 4 Å molecular sieves and a condenser mounted atop the Soxlet extractor. The solution was refluxed for 24 h with the condensed solvent passing through the bed of molecular sieves and was returned to the flask. Ethanol was removed by evaporation under vacuum, giving a residue. The residue was triturated with MTBE (50.0 ml) for two hours. The solid was filtered and dried at 50° C. under 10 mm Hg vacuum to afford amorphous pantoprazole sodium.

Example 3

Pantoprazole sodium Form II (5.0 g) was dissolved in acetonitrile (25 ml) at room temperature. MTBE (250 ml) was then slowly added. The solution was allowed to stand at room temperature for two days, giving the crystallized product. The precipitate was filtered and dried at 65° C. for two hours under ambient pressure to afford a mixture of pantoprazole sodium monohydrate and amorphous pantoprazole sodium.

Example 4

Pantoprazole sodium sesquihydrate was dried at 100° C. under 10 mm vacuum overnight, giving amorphous pantoprazole sodium.

Example 5

A 100 ml flask was charged with toluene (50.0 ml). Pantoprazole (5.0 g, 12.8 mmol) and 47% aqueous NaOH (1.2 g) were added to the stirred solvent at room temperature. The mixture was stirred until dissolution and then overnight until precipitation. The solid was filtered giving pantoprazole sodium. The sample was dried at 45° C. under 10 mm Hg vacuum overnight, giving 4.21 g of amorphous pantoprazole sodium.

Preparation of Pantoprazole Sodium Acetone Solvate Form IV

Example 6

Pantoprazole sodium Form II (5.0 g) in acetone (50 ml) was stirred at room temperature for 24 h to give a pantoprazole sodium solvate with acetone that has been denominated pantoprazole sodium Form IV.

Example 7

Pantoprazole sodium Form II (2.0 g) and acetone (0.4 ml) were subjected to rotary mixing in a rotary evaporator without vacuum at room temperature for two hours to afford pantoprazole sodium Form IV.

Example 8

Exposing pantoprazole sodium Form II (1.0 g) to acetone vapors in a sealed vessel at room temperature for two weeks afforded pantoprazole sodium Form IV.

Example 9

Pantoprazole sodium Form II (5.0 g) was dissolved in acetone (50 ml) by heating at reflux. After cooling to room temperature the mixture was stirred overnight. The crystals were filtered and analyzed by PXRD and TGA which showed that they were pantoprazole sodium Form IV. Drying of Form IV at 50° C. under vacuum at 10 mm Hg vacuum overnight yielded pantoprazole sodium Form I.

Example 10

Stirring amorphous pantoprazole sodium (1.6 g) in excess acetone (3.2 ml) at room temperature for two hours and filtering to remove excess acetone afforded pantoprazole sodium Form IV.

Preparation of Pantoprazole Sodium 1-Butanol Solvate Form V

Example 11

Pantoprazole (5.0 g, 12.8 mmol) and 98.5% NaOH (0.52 g, 12.8 mmol) were dissolved in 1-butanol (10.0 ml) at room temperature and the solution was stirred overnight at room temperature. The solution was cooled in a refrigerator and then stirred at room temperature until crystallization occurred. The crystals were filtered and dried at 50° C. under 10 mm Hg vacuum overnight to afford pantoprazole sodium Form V as determined by PXRD.

Example 12

Exposing pantoprazole sodium Form II (1.0 g) to 1-butanol vapors in a sealed vessel at room temperature for two weeks also affords pantoprazole sodium Form V.

The procedure described in Example 34 also affords pantoprazole sodium Form V.

Preparation of Pantoprazole Sodium Form VI

Example 13

Exposing pantoprazole sodium Form II (1.0 g) to water vapors in a sealed vessel at room temperature for two weeks affords pantoprazole sodium in novel Form VI.

The procedure set out in Example 35 also affords pantoprazole sodium Form VI.

Preparation of Pantoprazole Sodium Methyl Ethyl Ketone Solvate Form VIII

Example 14

Pantoprazole sodium monohydrate Form II (5.0 g) was slurried in MEK (50 ml) at room temperature for 24 h. The crystals were filtered and analyzed by PXRD and TGA which showed that they were a methyl ethyl ketone solvate that has been denominated Form VIII.

Example 15

Pantoprazole sodium Form II (1.0 g) and MEK (0.4 ml) were subjected to rotary mixing in a rotary evaporator without vacuum at room temperature for two hours to afford pantoprazole sodium Form VIII.

Example 16

Pantoprazole sodium Form II (5.0 g) was dissolved in MEK (50 ml) by heating at reflux. After cooling to room temperature the mixture was stirred overnight. The crystals were filtered and analyzed by PXRD and TGA which showed that they were a MEK solvate. Drying the crystals at 50° C. under vacuum at 10 mm Hg vacuum yielded pantoprazole sodium Form I.

Preparation of Pantoprazole Sodium Dimethylcarbonate Solvate Form IX

Example 17

Pantoprazole sodium Form II (5.0 g) was slurried with dimethylcarbonate (50 ml) at room temperature for 24 h. The crystals were filtered and analyzed by PXRD and TGA which showed that they were a pantoprazole sodium solvate with dimethylcarbonate which has been denominated Form IX.

Preparation of Pantoprazole Sodium Solvate with 1-Propanol Form X

Example 18

Pantoprazole (5.0 g, 12.8 mmol) and solid 98.5% NaOH (0.52 g, 12.8 mmol) were dissolved in 1-propanol (10 ml) at room temperature. MTBE (20.0 m) was then added and the mixture was placed in a freezer overnight. The precipitated crystals were filtered and analyzed by PXRD and TGA which showed them to be a solvate of pantoprazole sodium and 1-propanol which has been denominated Form X.

Preparation of Anhydrous Pantoprazole Sodium Form XI

Example 19

Pantoprazole sodium Form II (15.0 g) was dissolved in absolute methanol (75 ml). The solution was dried over 4 Å molecular sieves overnight. The solution was separated from the molecular sieves and the methanol was evaporated at reduced pressure. The oily residue was triturated with acetone (50 ml) at room temperature for 4 h and then placed in a refrigerator. The solid was filtered and analyzed by PXRD and TGA which showed that it was an anhydrous form of pantoprazole sodium, which has been denominated Form XI.

Preparation of Pantoprazole Sodium Solvate with 2-methylpropanol Form XII

Example 20

Pantoprazole sodium Form II (5.0 g) was dissolved in 2-methylpropanol (10 ml) by heating at reflux. The solution was allowed to stand at room temperature overnight. The crystals were filtered and analyzed by PXRD and TGA which showed them to be a pantoprazole sodium solvated with 2-methylpropanol which has been denominated Form XII. Drying of Form XII at 65° C. under ambient pressure for two hours yield pantoprazole sodium Form XIII.

Example 21

Pantoprazole sodium Form II (5.0 g) was dissolved in 2-methylpropanol (5 ml) by heating at reflux. The solution was allowed to stand at room temperature overnight. The crystals were filtered and analyzed by PXRD and TGA which showed them to be a pantoprazole sodium Form XII.

Preparation of Pantoprazole Sodium Form XIII

Drying pantoprazole sodium 1-butanol solvate prepared as described in Example 34 or pantoprazole sodium 2-methylpropanol solvate prepared as described in Example 20 at 65° C. under ambient pressure for two hours affords pantoprazole sodium Form XIII.

Example 22

Pantoprazole sodium Form II (5.0 g) was dissolved in acetone (10.0 ml) by heating at reflux. After a few minutes, the product was crystallized at once. The mixture was allowed to stand at room temperature overnight. The crystals were filtered and analyzed by PXRD which showed them to be novel pantoprazole sodium Form XIII.

Example 23

Pantoprazole sodium Form II (5.0 g) was dissolved in MEK (10 ml) by heating at reflux. The solution stood at room temperature overnight, giving the crystals. The crystals were filtered and determined to be pantoprazole sodium Form XIII by PXRD.

Preparation of Pantoprazole Sodium Hydrate Form XIV

Example 24

Pantoprazole sodium Form II (1.0 g) was put in a glass beaker, which was introduced into a bigger closed vessel (the vessel volume 125 ml), containing 20 ml of n-propanol and stored at room temperature. After 1 month crystals were obtained. The solid was filtered giving Pantoprazole Sodium Form XIV. The sample was dried at 50° C. under 10 mm Hg vacuum overnight giving pantoprazole sodium Form XV.

Preparation of Pantoprazole Sodium Hydrate Form XV

Example 25

Pantoprazole sodium (5.0 g) was dissolved in n-propanol (5 ml) by heating at reflux. Then, the solution was cooled to room temperature and the crystals of pantoprazole sodium Form XIV prepared as described in Example 24 were added for seeding without stirring. After 3 hours the obtained crystals were filtered giving wet Pantoprazole Sodium form XIV. The sample was dried at 50° C. under 10 mm Hg vacuum overnight giving pantoprazole sodium Form XV.

Preparation of Pantoprazole Sodium Hydrate Form XVI

Example 26

A 100 ml flask was charged with toluene (50.0 ml). Pantoprazole (5.0 g, 12.8 mmol) and solid 98.5% NaOH (0.575 g, 14.6 mmol) were added to the stirred solvent at room temperature followed by methanol (2 ml). The mixture was stirred until dissolution and then overnight until precipitation. The solid was filtered giving pantoprazole giving pantoprazole sodium Form XVI (4.65 g).

Preparation of Pantoprazole Sodium Form XVII

Example 27

Amorphous Pantoprazole sodium (1 g) was slurried in MEK (5 ml) at 25° C. for 1 hr. The suspension was stirred at 750 to 1200 rpm for 24 hrs. The crystals were filtered and analyzed by PXRD showing a novel form of pantoprazole sodium form XVII.

Preparation of Pantoprazole Sodium Form XVIII

Example 28

Amorphous Pantoprazole sodium (4 g) was slurried in Acetone (4 ml) at room temperature for 1 hr. The crystals were filtered, and analyzed by PXRD as wet samples and after drying at 50° C. showing a novel form of pantoprazole sodium Form XVIII.

Preparation of Pantoprazole Sodium Form XIX

Example 29

Pantoprazole sodium amorphous (4 g) was dissolved in 8 ml water and stirred for 6 hrs. at room temperature. Water was removed by evaporation under vacuum giving a solid. The solid was then dried at 50° C.

Preparation of Pantoprazole Sodium Form XX

Example 30

Amorphous pantoprazole sodium (1.0 g) was stirred with a 20:1 toluene:water mixture at ambient temperature for 5 days. The resulting solid was filtered and dried under 10 mm Hg vacuum at 50° C. overnight.

Example 31

Amorphous pantoprazole sodium (1.0 g) was stirred with a 100:1 hexane:water mixture at ambient temperature for 5 days. The resulting solid was filtered and analyzed by PXRD as wet product and after drying in 10 mm Hg vacuum at 50° C. overnight.

Example 32

Amorphous pantoprazole sodium (1.0 g) was stirred with a 10:1 hexane:water mixture at ambient temperature for 5 days. The solid was filtered and analyzed by PXRD as wet product and after drying in 10 mm Hg vacuum at 50° C. overnight.

Example 33

Pantoprazole sodium Form II (1.0 g) was stirred with a 20:1 toluene:water mixture at ambient temperature for 5 days. The solid was filtered and analyzed by PXRD as wet product and after drying in 10 mm Hg vacuum at 50° C. overnight.

Thermal Interconversion of Pantoprazole Sodium Solvates and Polymorphic Forms

Example 34

Pantoprazole sodium Form II (5.0 g) was dissolved in 1-butanol (10.0 ml) by heating to reflux. The mixture was stirred overnight at ambient temperature, giving the crystals. The crystals were filtered on filter paper. PXRD analysis showed that the undried crystals were pantoprazole sodium Form V.

Pantoprazole sodium Form V was dried at 65° C. under ambient pressure for two hours. PXRD analysis of the dried crystals showed that they pantoprazole sodium Form XIII.

When the pantoprazole sodium Form XIII was dried at 65° C. for another two hours under ambient pressure, the product was partially amorphous.

Example 35

Pantoprazole sodium Form II (5.0 g) was dissolved in a 1:1 methanol:water mixture (10 ml) at room temperature. The solution was stirred overnight without precipitation. The solution was allowed to stand overnight in an opened flask with precipitation of the product. The crystals were filtered and allowed to stand at room temperature open to the air for a short period of time but were not otherwise dried. PXRD analysis of the crystals revealed that they were pantoprazole sodium Form VI.

The pantoprazole sodium Form VI was then dried at 50° C. under a 10 mm Hg vacuum overnight. The resulting powder was analyzed by PXRD and found to be amorphous.

Example 36

Pantoprazole sodium Form II (5.0 g) was dissolved in acetone (10.0 ml) by heating at reflux. The mixture was allowed to cool overnight and the crystals were filtered the next day and analyzed by PXRD, which revealed that they were pantoprazole sodium monohydrate Form XIII. When the crystals were dried at 65° C. for two hours under ambient pressure they converted into amorphous pantoprazole sodium.

Preparation of Pantoprazole Sodium Monohydrate

Example 37

Pantoprazole sodium Form II (5.0 g) was added to THF (5.0 ml) and heated to reflux until completely dissolved. The solution was left uncovered overnight at ambient temperature giving the crystals. The crystals were collected on filter paper and dried at 65° C. for two hours under ambient pressure. The crystals were determined by Karl Fisher analysis and PXRD to be the monohydrate.

Example 38

Pantoprazole sodium Form II (5.0 g) was dissolved in methanol (25.0 ml) at room temperature. MTBE (500 ml) was then slowly added to the solution. The morning of the next day the crystals were filtered and dried at 65° C. for two hours under ambient pressure. The crystals were determined by Karl Fisher analysis and PXRD to be the monohydrate.

Example 39

Pantoprazole sodium Form II (5.0 g) was dissolved in 2-propanol (50.0 ml) at room temperature. Cyclohexane (20 ml) was then slowly added to the solution. Pantoprazole sodium initially was separated as an oil, but after the mixture was allowed to stand at room temperature in an opened flask for a week the oil had transformed to crystals. The crystals were filtered and dried at 65° C. for two hours under ambient pressure. The crystals were determined by Karl Fisher analysis and PXRD to be the monohydrate.

Example 40

Pantoprazole sodium Form II (5.0 g) was dissolved in acetonitrile (25.0 ml) at room temperature. Toluene (250 ml) was then slowly added to the solution. Pantoprazole sodium initially was separated as an oil, but after the mixture was allowed to stand at room temperature in an open flask for two days the oil had transformed to crystals. The crystals were filtered and dried at 65° C. for two hours under ambient pressure. The crystals were determined by Karl Fisher analysis and PXRD to be the monohydrate.

Example 41

Pantoprazole sodium Form II (5.0 g) was dissolved in acetonitrile (25.0 ml) at room temperature. MTBE (250 ml) was then slowly added to the solution. The mixture was allowed to stand for two days, giving the crystals. The crystals were filtered and dried at 65° C. for two hours under ambient pressure. The crystals were determined by Karl Fisher analysis and PXRD to be the monohydrate.

Example 42

Pantoprazole sodium Form II (5.0 g) was dissolved in 1-propanol (5.0 ml) by heating at reflux. The mixture was allowed to stand overnight at ambient temperature and in the morning, the crystals were filtered and dried at 50° C. under 10 mm Hg vacuum overnight. The crystals were determined by Karl Fisher analysis and PXRD to be the monohydrate.

Example 43

Pantoprazole sodium Form II (5.0 g) was added to dimethylcarbonate (5.0 ml) at room temperature. The suspension was stirred at room temperature for 24 h. The crystals were separated from the dimethylcarbonate by filtration and were dried at 50° C. under 10 mm Hg vacuum overnight. The crystals were determined by Karl Fisher analysis and PXRD to be the monohydrate.

Example 44

Pantoprazole (5.0 g, 12.8 mmol) and solid 98.5% NaOH (0.52 g, 12.8 mmol) was added to 1-propanol (10 ml) and stirred at room temperature until the NaOH completely dissolved. MTBE (20.0 ml) was then slowly added. Upon completing the addition, the solution was placed in a freezer overnight, giving the crystals. The crystals were filtered and dried at 50° C. under 10 mm Hg vacuum overnight. The crystals were determined by Karl Fisher analysis and PXRD to be the monohydrate.

Example 45

Amorphous pantoprazole sodium (1.6 g) was added to acetone (3.2 ml) at room temperature. The suspension was stirred at room temperature for 2 h. The solid was filtered and dried at 50° C. under 10 mm Hg vacuum overnight. The crystals were determined by Karl Fisher analysis and PXRD to be the monohydrate.

Example 46

Pantoprazole sodium sesquihydrate (5.0 g) was added to dimethylcarbonate (50 ml). The suspension was stirred for three days at room temperature. The crystals were filtered and dried at 50° C. under 10 mm Hg vacuum overnight. The crystals were determined by Karl Fisher analysis and PXRD to be the monohydrate.

Preparation of Pantoprazole Sodium Sesquihydrate

Example 47

Pantoprazole sodium Form II (5.0 g) was dissolved in 2-propanol (5.0 ml) by heating at reflux. After standing overnight at room temperature the mixture remained a clear solution. The solvent was allowed to evaporate while the mixture was allowed to stand uncovered at room temperature for another night. The crystals were filtered and dried at 65° C. under ambient pressure for two hours. The crystals were determined by Karl Fisher analysis and PXRD to be the sesquihydrate.

Example 48

Pantoprazole sodium Form II (5.0 g) was dissolved in THF (10.0 ml) by heating at reflux. The solution was stirred overnight in a closed flask at ambient temperature. No crystals had formed by the next day, so the solution was allowed to stand another night in an opened flask. This time, crystals formed in the flask. The crystals were filtered on filter paper and dried at 65° C. under ambient pressure for two hours. The crystals were determined by Karl Fisher analysis and PXRD to be the sesquihydrate.

Example 49

Pantoprazole sodium Form II (5.0 g) was dissolved in acetonitrile (5.0 ml) by heating at reflux. The solution was stirred overnight in a closed flask at ambient temperature giving the crystals. The crystals were filtered and dried at 65° C. under ambient pressure for two hours. The crystals were determined by Karl Fisher analysis and PXRD to be the sesquihydrate.

Example 50

Pantoprazole sodium Form II (5.0 g) was dissolved in ethanol (5.0 ml) by heating at reflux. The solution was stirred overnight in a closed flask at ambient temperature. No crystals formed. Heptane (5.0 ml) was added to the solution and the mixture was again stirred overnight. Again, no crystals formed. Finally, the flask was opened and the solution was left exposed to the atmosphere for another night. The precipitated crystals were filtered and dried at 65° C. under ambient pressure for two hours. The crystals were determined by Karl Fisher analysis and PXRD to be the sesquihydrate.

Example 51

Pantoprazole sodium Form II (5.0 g) was dissolved in water (5.0 ml) by heating at reflux. The solution was stirred overnight in a closed flask at ambient temperature. No crystals formed. The flask was opened and the solution was left exposed to the atmosphere for another night. The precipitated crystals were filtered and dried at 50° C. under 10 mm Hg vacuum overnight. The crystals were determined by Karl Fisher analysis and PXRD to be the sesquihydrate.

Example 52

Pantoprazole sodium Form II (5.0 g) was dissolved in a 5:4 mixture of sec-butanol:dichloromethane (90 ml) at room temperature. The solution was stirred overnight in a closed flask without a change in appearance. The flask was opened and the solution was left exposed to the atmosphere for another night. The crystals were filtered and dried at 50° C. under 10 mm Hg vacuum overnight. The crystals were determined by Karl Fisher analysis and PXRD to be the sesquihydrate.

Example 53

Pantoprazole sodium Form II (5.0 g) was dissolved in ethyl acetate (50.0 ml) by heating at reflux. The solution was stirred overnight in a closed flask at ambient temperature. No crystals formed. The solution was then concentrated to about 5 ml. The concentrated solution was left in an uncovered flask for another night, giving the crystals The crystals were filtered and dried at 65° C. under ambient pressure. The crystals were determined by Karl Fisher analysis and PXRD to be the sesquihydrate.

Example 54

Pantoprazole sodium Form II (5.0 g) was added to ethyl acetate (50.0 ml) at room temperature. The suspension was stirred at room temperature for 24 h. The crystals were filtered and dried at 50° C. under 10 mm Hg vacuum overnight. The crystals were determined by Karl Fisher analysis and PXRD to be the sesquihydrate.

Example 55

Pantoprazole sodium Form II (5.0 g) was added to dichloromethane (50.0 ml) at room temperature. The heterogeneous mixture was stirred at room temperature for 24 h. The crystals were filtered and dried at 50° C. under 10 mm Hg vacuum overnight. The crystals were determined by Karl Fisher analysis and PXRD to be the sesquihydrate.

Example 56

Pantoprazole sodium Form II (5.0 g) was added to water (5.0 ml) at room temperature. The suspension was stirred at room temperature for 24 h. The crystals were filtered and dried at 50° C. under 10 mm Hg vacuum overnight. The crystals were determined by Karl Fisher analysis and PXRD to be the sesquihydrate.

Example 57

Pantoprazole sodium Form I (5.0 g) was added to dimethylcarbonate (50.0 ml) at room temperature. The suspension was stirred at room temperature for 24 h. The crystals were filtered and dried at 50° C. under 10 mm Hg vacuum overnight. The crystals were determined by Karl Fisher analysis and PXRD to be the sesquihydrate.

Example 58

Pantoprazole sodium Form II (5.0 g) and water (0.4 ml) were subjected to rotary mixing in a rotary evaporator without vacuum at room temperature for two hours. The crystals were determined by Karl Fisher analysis and PXRD to be the sesquihydrate.

Example 59

Pantoprazole sodium Form II (5.0 g) and a 1:1 mixture of 2-propanol:water (0.4 ml) were subjected to rotary mixing in a rotary evaporator without vacuum at room temperature for two hours. The crystals were determined by Karl Fisher analysis and PXRD to be the sesquihydrate.

Example 60

Pantoprazole sodium Form II (1.0 g) was placed in glass which was put into a 125 ml closed vessel containing 20 ml of ethyl acetate. The pantoprazole sodium was exposed to the ethyl acetate vapors for two weeks at ambient temperature giving the crystals which were analyzed by Karl Fisher analysis technique and PXRD and found be the sesquihydrate.

Example 61

Pantoprazole (5.0 g, 12.8 mmol) and solid 98.5% NaOH (0.52 g, 12.8 mmol) were added to methanol (10 ml) and stirred at room temperature until the NaOH was completely dissolved. The mixture was stirred overnight in a closed flask. No crystals formed. The flask was opened and the solution was stirred overnight. No crystals had formed by the next day. MTBE (50 ml) was added to the mixture. The mixture was stirred for two hours, giving the crystals. The crystals were isolated by filtration and dried at 50° C. under 10 mm Hg vacuum overnight. The dried crystals were determined by Karl Fisher analysis to be the sesquihydrate.

Example 62

Pantoprazole (5.0 g, 12.8 mmol) and solid 98.5% NaOH (0.52 g, 12.8 mmol) were added to ethanol (10 ml) and stirred at room temperature until the NaOH was completely dissolved. The mixture was stirred overnight in a closed flask. No crystals formed. The flask was opened to the air and the solution was stirred overnight. No crystals had formed by the next day. MTBE (50 ml) was added to the mixture. The mixture was stirred for two hours, giving the crystals. The crystals were isolated by filtration and dried at 50° C. under 10 mm Hg vacuum overnight. The dried crystals were determined by Karl Fisher analysis to be the sesquihydrate.

Example 63

Pantoprazole (5.0 g, 12.8 mmol) and solid 98.5% NaOH (0.52 g, 12.8 mmol) were added to 2-propanol (10 ml) and stirred at room temperature until the NaOH was completely dissolved. The mixture was stirred overnight in a closed flask. No crystals formed. MTBE (20 ml) was added to the mixture. The mixture was stirred overnight, but no crystals formed. The mixture was then stirred overnight in an opened flask, giving the crystals. The crystals were isolated by filtration and dried at 50° C. under 10 mm Hg vacuum overnight. The dried crystals were determined by Karl Fisher analysis to be the sesquihydrate.

Example 64

Pantoprazole (5.0 g, 12.8 mmol) and solid 98.5% NaOH (0.52 g, 12.8 mmol) were added to sec-butanol (10 ml) and stirred at room temperature until the NaOH was completely dissolved. The mixture was stirred overnight in a closed flask. No crystals formed. MTBE (20 ml) was added to the mixture. The mixture was then stirred overnight in an open flask, giving the crystals. The crystals were isolated by filtration and dried at 50° C. under 10 mm Hg vacuum overnight. The dried crystals were determined by Karl Fisher analysis to be the sesquihydrate.

Having thus described the invention with respect to certain preferred embodiments and further illustrated it with examples, those skilled in the art may come to appreciate substitutions and equivalents that albeit not expressly described are taught and inspired by this invention. Whereas such substitutions and equivalents do not depart from the spirit of the invention they are within its scope which is defined by the claims that follow.

What is claimed is:

1. A process for preparing pantoprazole sodium sesquihydrate comprising: a) adding pantoprazole and a source of sodium ions to a diluent selected from the group consisting of 2-propanol, tetrahydrofuran, acetonitrile, methanol, ethanol, water, mixtures of sec-butanol and dichloromethane, and ethyl acetate, and b) crystallizing pantoprazole sodium sesquihydrate from the obtained mixture, and c) isolating the crystals from the diluent.

2. The process of claim 1 wherein the diluent is selected from the group consisting of methanol and ethanol.

3. The process of claim 1 wherein the source of sodium ions is a mixture of sodium hydroxide and water.

4. The process of claim 1 wherein a solution is formed by dissolving the pantoprazole in the diluent, followed by adding the source of sodium ions, wherein the source of sodium ions is in solution in the diluent.

5. The process of claim 1, wherein adding in step a) forms a solution and the mixture in step b) is a solution.

6. The process of claim 1, wherein crystallization is induced by adding an anti-solvent to the mixture in step b).

7. The process of claim 6, wherein the anti-solvent is selected from the group consisting of heptane and MTBE.

* * * * *